United States Patent
Thoonen et al.

(10) Patent No.: US 8,026,417 B2
(45) Date of Patent: Sep. 27, 2011

(54) **HIGH OIL HYBRID *BRASSICA* LINE 46P50**

(75) Inventors: Ferdinand G. Thoonen, Guelph (CA);
Jayantilal D. Patel, Thornhill (CA);
Winnifred Marie McNabb, Manitou (CA); Wayne R. Leitch, Georgetown (CA)

(73) Assignee: Pioneer Hi Bred International Inc, Johnston, IA (US)

( * ) Notice: Subject to any disclaimer, the term of this patent is extended or adjusted under 35 U.S.C. 154(b) by 1069 days.

(21) Appl. No.: 11/739,384

(22) Filed: Apr. 24, 2007

(65) Prior Publication Data

US 2008/0271198 A1    Oct. 30, 2008

(51) Int. Cl.
*A01H 5/00* (2006.01)

(52) U.S. Cl. .......................... 800/306; 800/264

(58) Field of Classification Search .......... None
See application file for complete search history.

(56) References Cited

U.S. PATENT DOCUMENTS

| 6,720,481 B1 | 4/2004 | Patel et al. |
| 6,936,751 B2 * | 8/2005 | Charne et al. ................. 800/306 |

FOREIGN PATENT DOCUMENTS

WO    2007016521 A2    2/2007

OTHER PUBLICATIONS

"Agricore United Accesses Exclusive Pioneer 'R' Brand Canola Products"; Market Wire, May 2006, pp. 1-2; BNET Business Network; Retrieved from the Internet: URL: http//findarticles.com/p/articles/mi_pwwi/is_200605/al_n1634907/pg_1>.
Seedquest, Nov. 15, 2006; Retrieved from the Internet: URL: http://www.seedquest.com/News/releases/2006/november/17548.htm>.

* cited by examiner

*Primary Examiner* — Elizabeth McElwain

(57) ABSTRACT

An improved *Brassica* hybrid plant and seed thereof designated 46P50 are provided. The *Brassica* hybrid produces seed having an average weight of oil per gram of mature dried seed that is between about 2.7 to 3.3 percentage points higher than that produced by current commercial hybrids when grown under the same environmental conditions. Also provided are methods for producing the hybrid plant, methods of oil and meal production, and methods of breeding with the hybrid plant.

23 Claims, 3 Drawing Sheets

HIGH OIL HYBRID *BRASSICA* LINE 46P50

FIELD OF INVENTION

The invention relates to *Brassica* hybrid breeding, and in particular high oil *Brassica* hybrids.

BACKGROUND

*Brassica* species are increasingly important oilseed crops in many parts of the world. As a source of vegetable oil, *Brassica* presently ranks behind only soybeans and palm and is virtually tied with sunflowers for the number three position of commercial importance. The oil is used both as a salad oil and as a cooking oil throughout much of the world.

In its original form *Brassica* oil, often known as rapeseed oil, was found to have deleterious effects on human health due to its relatively high level of erucic acid which commonly is present in native cultivars in concentrations of 30 to 50 percent by weight based upon the total fatty acid content. Plant scientists identified a source of low erucic acid germplasm and used this germplasm to breed low erucic acid cultivars (Chapter 6 entitled "The Development of Improved Rapeseed Cultivars" by B. R. Stefansson from "High and Low Erucic Acid Rapeseed Oils" edited by John K. G. Kramer, Frank D. Sauer, and Wallace J. Pigden, Academic Press Canada (1983)).

In Canada, plant scientists focused their efforts on creating "double-low" varieties which were low in erucic acid in the oil and low in glucosinolates in the solid meal remaining after oil extraction (i.e., an erucic acid content of less than 2 percent by weight based upon the total fatty acid content, and a glucosinolate content of less than 30 micromoles per gram of the oil-free meal). These higher quality forms of rape developed in Canada are known as canola. In contrast, European scientists worked to achieve only "single-low" types which were low in erucic acid, but did not attempt to improve the quality of the solid meal which retained a glucosinolate content of about 100 micromoles per gram of oil-free meal.

The result of this major change in the fatty acid composition of rapeseed oil was the creation of a new oil profile which often contained approximately 8 to 15 percent by weight of alpha-linolenic acid, approximately 62 percent by weight of oleic acid based upon the total fatty acid content, and approximately 7 percent or more by weight of saturated fatty acids in the form of lauric acid (C12:0), myristic acid (C14:0), palmitic acid (C16:0), stearic acid (C18:0), arachidic acid (C20:0), behenic acid (C22:0) and lignoceric acid (C24:0) based upon the total fatty acid content. Since the overall percentage of oil in the seed did not change appreciably when the new low erucic cultivars were developed, it appeared that the erucic acid oil component had been redirected into other fatty acids within the oil (Chapter 7 entitled "The Introduction of Low Erucic Acid Rapeseed Varieties Into Canadian Production" by J. K. Daun from the previously identified Academic Press Canada (1983) publication; "Prospects for the Development of Rapeseed (*B. napus* L.) With Improved Linoleic and Linolenic Acid Content" by N. N. Roy and A. W. Tarr, (1987) *Plant Breeding* 98:89-96; and "Genetic Control of Fatty Acid Composition in Oilseed Crops" by R. K. Downey and D. G. Dorrell, *Proc. Flax Inst. U.S.A.* 47(3)1-3).

Canola oil presently consists of approximately 7 percent saturated fatty acids primarily in the form of stearic acid (C18:0) and palmitic acid (C16:0), approximately 62 percent by weight oleic acid (C18:1) which contains a single double bond per molecule, approximately 21 percent by weight linoleic acid (C18:2) which contains two double bonds per molecule, approximately 10 percent by weight linolenic acid (C18:3) which contains three double bonds per molecule, and less than one percent by weight erucic acid (C22:1) which contains a single double bond per molecule.

Over the years scientists have attempted to improve the fatty acids profile for canola oil (for example, Chapter 10 by Gerhard Röbbelen entitled "Changes and Limitations of Breeding for Improved Polyenic Fatty Acids Content in Rapeseed" from "Biotechnology for the Oils and Fats Industry" edited by Colin Ratledge, Peter Dawson, and James Rattray, American Oil Chemists' Society (1984)). Further, scientists have been attempting to increase the overall oil content of the seed. FIG. 1 shows the steady rise in oil content of Canadian canola cultivars over the past 20 years.

In addition to high oil, the plant must also exhibit optimum agronomic performance. Such agronomic performance includes excellent vigor, flowering propensity, number of pods per plant, number of seeds per pod, plant yield, disease resistance and herbicide resistance. In order to produce high yielding lines that can compete with current commercial lines, hybrid performance is required. High oil content in the seed combined with a high yield per hectare, makes possible a very high oil yield per hectare.

The production of *Brassica* hybrids is challenging because *Brassica* plants, and in particular *Brassica napus* plants, are generally able to self pollinate, as both male and female sexual organs are present in each flower. Accordingly, a hybrid system is required. There are several hybrid systems available in *Brassica*, each with advantages and disadvantages. These include: (i) self incompatibility (SI), (ii) genetic male sterility (GMS), and (iii) cytoplasmic male sterility (CMS). In addition, there are several CMS systems available in *Brassica*, the most common being Ogura CMS.

In CMS systems, including Ogura CMS, the female line (A line) is male sterile by virtue of a mutation in the DNA of the mitochondria. The male line (also called the restorer line or R line) contains a restorer gene in the nuclear genome that restores male fertility in Ogura CMS plants. Restorer lines for Ogura CMS lines were originally available from Institut National de Recherche Agrocole (INRA) of Rennes, France (WO92/05251 and WO98/027806, which are herein incorporated by reference). A third line, the maintainer line or B line, is required to propagate the male sterile female line. This line is generally isogenic to the male sterile female line and differs only in the cytoplasm. A hybrid plant is produced when the female CMS line is pollinated by the male restorer line and seed is harvested from the female line. Accordingly, the genotype and the phenotype of the resulting hybrid seed and plant are determined by the genetics of the female and male parents. If the male restorer plant comprises a homozygous restorer gene, then every F1 hybrid seed will be fully restored and fertile. If the male restorer plant comprises a heterozygous restorer gene, then 50% of the F1 hybrid seed will be fully restored and fertile and 50% will be male sterile.

In Canada, *Brassica* grain is used primarily for oil production, as approximately 40-45% of the crushed seed is oil. There have been many attempts to alter the fatty acid profile of the oil as well as to increase the overall oil content. A higher oil yielding line could exact a premium for growers. Enhancing the oil content while simultaneously improving grain yield and agronomic traits is a major challenge for breeders (D. Hauska, C. Oertel, L. Alpmann, D. Stelling, H. Busch (2007) In Proceeding of $12^{th}$ International Rapeseed Congress. Science Press USA Inc. NJ 08852, USA. pp 159-162). However, the combination of very high oil, very high grain yield, excellent agronomic performance and disease resistance in a cultivar has not been found in *Brassica napus* in nature, despite many years of evolution. In addition, the combination of high oil and excellent agronomic performance has not been developed in *Brassica napus* by man, despite over 35 years of active canola breeding in Western Canada, Europe, and Australia.

SUMMARY OF THE INVENTION

The present invention relates to a new and distinctive *Brassica* hybrid which is the result of years of careful breeding and selection.

These and other features of the Applicant's teachings are set forth herein.

DEFINITIONS

Figure 1:
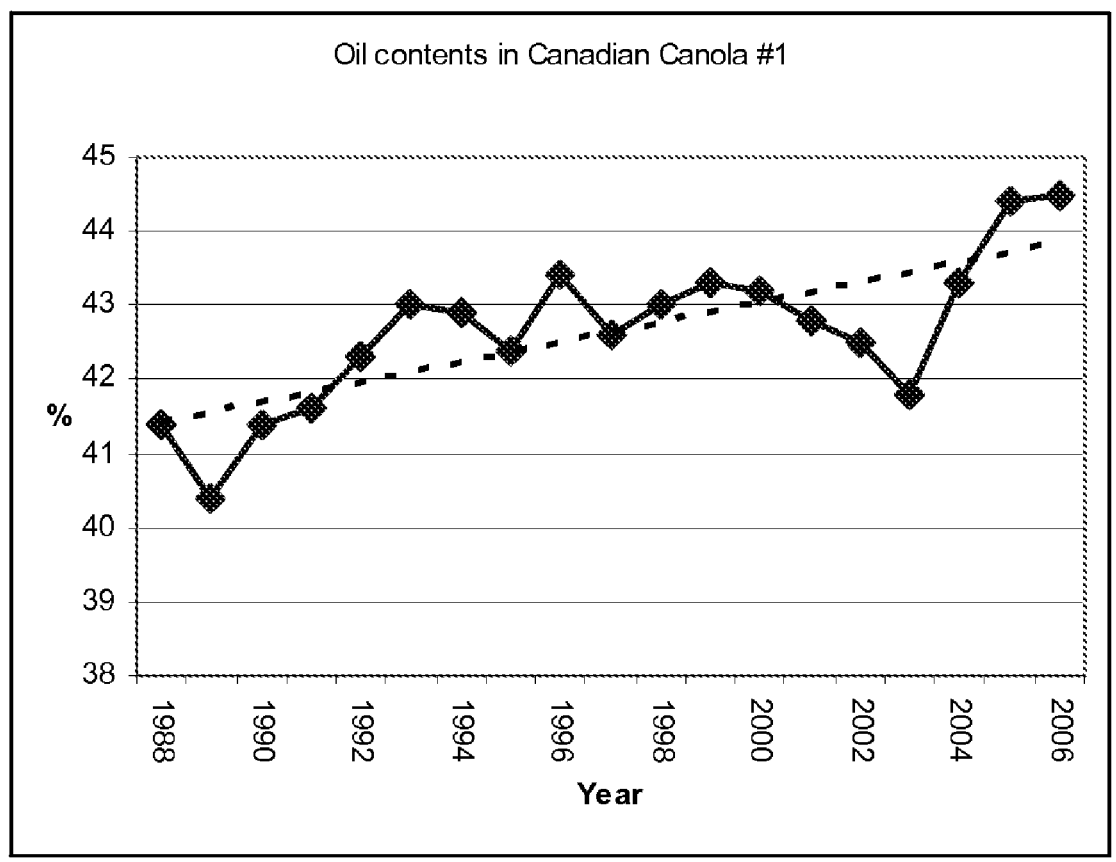
FIG. 1: Oil contents (%) in Canadian canola crop (Canada #1) from 1988 to 2006 expressed at 8.5% moisture (source—Canadian Grain Commission).

In the description and tables which follow a number of terms are used. In order to aid in a clear and consistent understanding of the specification the following definitions and evaluation criteria are provided.

Agronomic Score at Maturity: This is a visual score assigned by a trained individual in the field of field canola breeding while evaluating large number of progenies for the purpose of selection at physiological maturity. At this stage, each line would show clear differences due to different color of pods, different pod angle, pod density, plant height, branching pattern etc. The purpose is to assess the overall yield potential of a line by visually observing yield contributing traits such as number of pods per plant, length of pods, pod density on main raceme, number of primary and secondary branches, etc. Understanding the relationship between yield contributing traits is important. For example, number of pods per plant on the main raceme is a trait which has a strong correlation with yield but as the number of pods per plant increases, the length of pod decreases. The agronomic score is assigned from 9 to 1 where the lines with 9 would appear to be highest yielding while 1 would appear to be lowest yielding based on visual appearance.

Agronomic Score at Flowering: This is a visual score assigned by a trained individual in the field of canola breeding while evaluating a large number of canola lines for the purpose of selection at mid to late flowering. Number of pods per plant has a strong correlation with yield; therefore, the idea is to assess the number of pods based on number of open flowers, number of pods which are already formed and number of buds which are yet to open. Also, the density of pods and flowers and length of the main raceme is taken into consideration. The agronomic score at flowering is assigned from 9 to 1 where the lines with 9 would appear to have long main raceme, lots of secondary branches, high density of flowers and pods on the raceme and lots of buds yet to be open. The lines with a score of 1 would appear to be opposite of 9.

Type or Seasonal Type: This refers to whether the new cultivar is considered to be primarily a Spring or Winter type of canola.

Leaf Color: The leaf blade coloration is observed when at least 6 leaves of the plant are completely developed.

Leaf Glaucousity: The presence or absence of a fine whitish powdery coating on the surface of the leaves, and the degree thereof when present are observed.

Leaf Lobes: The fully developed upper stem leaves are observed for the presence or absence of leaf lobes when at least 6 leaves of the plant are completely developed.

Number of Leaf Lobes: The frequency of leaf lobes when present is observed when at least 6 leaves of the plant are completely developed.

Leaf Surface: The leaf surface is observed for the presence or absence of wrinkles when at least 6 leaves of the plant are completely developed.

Leaf Dentation: The margins of the upper stem leaves are observed for the presence or absence of indentation or serration, and the degree thereof if present when at least 6 leaves of the plant are completely developed.

Leaf Length: The length of the leaf blades and petioles are observed when at least 6, leaves of the plant are completely developed (mean of 50).

Leaf Width: The width of the leaf blades are observed when at least 6 leaves of the plant are completely developed (mean of 50).

Stem Anthocyanin Coloration: The presence or absence of leaf anthocyanin coloration and the intensity thereof if present are observed when the plant has reached the 9 to 11 leaf-stage.

Plant Height: The overall plant height at the end of flowering is observed (mean of 50).

Time of Flowering: A determination is made of the number of days from planting when at least 50 percent of the plants have one or more open buds on a terminal raceme in the year of sowing.

Flower Petal Coloration: The coloration of open exposed petals on the first day of flowering is observed.

Petal Length: The lengths of typical petals of fully opened flowers are observed (mean of 50).

Petal Width: The widths of typical petals of fully opened flowers are observed (mean of 50).

Pollen Formation or Anther Fertility: The relative level of pollen formation is observed at the time of dehiscence.

Pod or Silique Type: The overall configuration of the silique is observed.

Pod or Silique Length: The typical silique length is observed and is expressed on a scale of 1 (short) to 5 (long).

Pod or Silique Width: The typical silique width when mature is observed and is expressed on a scale of 1 (narrow) to 5 (wide).

Pedicel Length: The typical length of the silique peduncle when mature is observed and is expressed on a scale of 1 (short) to 5 (long).

Length of Beak: The typical length of the silique beak when mature is observed and is expressed on a scale of 1 (short) to 5 (long).

Maturity: The number of days from planting to maturity is observed with maturity being defined as the plant stage when pods with seed color change, occurring from green to brown or black, on the bottom third of the pod bearing area of the main stem.

Seeds Per Pod: The average number of seeds per pod is observed (mean of 50).

Seed Size: The weight in grams of 1,000 typical seeds is determined at maturity while such seeds exhibit a moisture content of approximately 7 to 9 percent by weight.

Seed Coat Color: The seed coat color of typical mature seeds is observed.

Seed Coat Mucilage: The presence or absence of mucilage on the seed coat is determined and is expressed on a scale of 1 (absent) to 9 (heavy). During such determination a petri dish is filled to a depth of 0.3 cm with tap water provided at room temperature. Seeds are added to the petri dish and are immersed in water where they are allowed to stand for five minutes. The contents of the petri dish containing the immersed seeds next is examined under a stereo microscope equipped with transmitted light. The presence of mucilage and the level thereof is observed as the intensity of a halo surrounding each seed.

NIR: Near Infra Red spectroscopy may be used to analyze oil content, protein content, chlorophyll content and total glucosinolate content (NIR (Near Infra Red spectroscopy) (P. C. Williams, 'Application of Near Infrared Reflectance Spectroscopy to Analysis of Cereal Grains and Oilseeds', Cereal Chem., 52:561-576 (1975), herein incorporated by reference). The individual samples are cleaned to remove dockage. The NIR instrument must be calibrated to and verified against the appropriate listed reference method.

Oil Content: The typical percentage by weight oil present in the mature whole dried seeds is determined by methods based on "AOCS Official Method Am 2-92 Oil content in Oilseeds". Analysis by pulsed NMR "ISO 10565:1993 Oilseeds Simultaneous determination of oil and water—Pulsed NMR method" or by NIR (Near Infra Red spectroscopy) (P. C. Williams, 'Application of Near Infrared Reflectance Spectroscopy to Analysis of Cereal Grains and Oilseeds', *Cereal Chem.* 52:561-576 (1975), herein incorporated by reference) are acceptable methods and data may be used for Canadian registration as long as the instruments are calibrated and certified by Grain Research Laboratory of Canada. Other methods as known to those skilled in the art may also be used. Percent oil is calculated as the weight of the oil divided by the weight of the seed at 0% moisture. Percent increase in oil content may be measured with reference to a check variety. For example, a 3% increase in oil content of Variety B over Variety A represents a difference in oil content of 3 percentage points when the weight of oil present in the mature dried seed of each variety is calculated.

Protein Content: The typical percentage by weight of protein in the oil free meal of the mature whole dried seeds is determined by methods based on "AOCS Official Method Ba 4e-93 Combustion Method for the Determination of Crude Protein". Protein can be analyzed using NIR (Near Infra Red spectroscopy), (P. C. Williams, 'Application of Near Infrared Reflectance Spectroscopy to Analysis of Cereal Grains and Oilseeds', *Cereal Chem.* 52:561-576 (1975) herein incorporated by reference). Data can be used for Canadian registration as long as the instruments are calibrated and certified by Grain Research Laboratory of Canada. Other methods known to those skilled in the art may also be used.

Fatty Acid Content: The typical percentages by weight of fatty acids present in the endogenously formed oil of the mature whole dried seeds are determined. During such determination the seeds are crushed and are extracted as fatty acid methyl esters following reaction with methanol and sodium methoxide. Next the resulting ester is analyzed for fatty acid content by gas liquid chromatography using a capillary column which allows separation on the basis of the degree of unsaturation and fatty acid chain length. This procedure is described in the work of J. K. Daun, et al., (1983) *J. Amer. Oil Chem. Soc.* 60:1751-1754 which is herein incorporated by reference.

Chlorophyll Content: The typical chlorophyll content of the mature seeds is determined by using methods based on "AOCS Official Method Ak2-92 Determination of chlorophyll content in rapeseed (Colza) by spectrophotometry", herein incorporated by reference. Chlorophyll can be analyzed using NIR (Near Infra Red spectroscopy) (R. Tkachuk, V. J. Mellish, J. K. Daun and L. J. Macri 'Determination of Chlorophyll in Ground Rapeseed Using a Modified Near Infrared Reflectance Spectrophotometer', *J. Am Oil Chem. Soc.* 65(3):381-385; herein incorporated by reference). Chlorophyll content is considered to be low if <8 ppm, medium if 8 to 15 ppm, and high if 15 to 30 ppm.

Glucosinolate Content: The total glucosinolates of seed at 8.5% moisture is measured by using methods based on "AOCS Official Method AK-1-92 (93) (Determination of glucosinolates content in rapeseed-colza by HPLC)"; herein incorporated by reference. NIR data can be used for Canadian registration as long as the instruments are calibrated and certified by Grain Research Laboratory of Canada. Glucosinolate content is expressed as micromoles per gram at 8.5% moisture.

Resistance to Shattering: Resistance to silique shattering is observed at seed maturity and is expressed on a scale of 1 (poor) to 5 (excellent).

Resistant to Lodging: Resistance to lodging is observed at seed maturity and is expressed on a scale of 1 (weak) to 5 (strong).

Blackleg Resistance: In trials run by the Applicant, a scale of 1-9 was used. A severely damaged plant with extensive internal necrosis and poor seed set was given a score of 1. If the stem was clean, green and no sign of disease or canker or damage was seen, a score of 9 was given. The data collected on single plants were averaged for each line in each replicate and statistical analysis was carried out. Overall score for the line was obtained by averaging over all replicates and locations. Tables 7, 8 and 9 were trials run by the Applicant and utilized a scale of 1 to 9, with 1 being poor and 9 being best. Data from other Blackleg resistance trials run by other parties is included in the Applicant's teachings. Tables 10 and 11 show the results of trials run by Western Canadian Canola/Rapeseed Recommending Committee (WCC/RRC) and utilized a blackleg scale of 0=good and 5=poor. Finally, Table 13 shows data for variety registration office trials, and utilized a scale of 1=resistant and 9=highly susceptible.

White Rust Resistance: For Table 14, plants were scored on a scale where 1=resistant, 9=highly susceptible Glyphosate Resistance: For Table 14, plants were scored on a scale of 1 to 9, with 1=resistant, 5=tolerant, 9=highly susceptible. A glyphosate resistant plant is resistant to glyphosate when applied at the recommended rate. The recommended application rate for glyphosate is 0.30 to 0.45 kilograms/hectare.

DESCRIPTION

*Brassica napus* is a dibasic allotetraploid formed of two genomes (i.e., the A-genome and C-genome) and has a total of 38 chromosomes. The A-genome component is derived from *Brassica campestris* and consists of 20 chromosomes. The C-genome component is derived from *Brassica oleracea* and consists of 18 chromosomes.

Plant Breeding

The goal of plant breeding is to combine in a single variety or hybrid various desirable traits of the parental lines. For field crops, these traits may include resistance to diseases and insects, resistance to herbicides, tolerance to heat and drought, reducing the time to crop maturity, greater yield, and better agronomic quality. Many crops, including *Brassicas*, are harvested mechanically and therefore require uniformity of plant characteristics such as germination and stand establishment, growth rate, maturity, and size. It is important to realize that many of these characteristics would not benefit wild-type plants found in nature, and have only been bred into cultivated plants by man to achieve the goal of feeding vast populations. For example, herbicide resistance is not generally found in nature, as only humans apply herbicides. Another example of traits introduced by human intervention is uniformity of germination and stand establishment, growth rate, maturity and size. These characteristics are important for commercial farming practices. For example, when applying herbicides or pesticides to plants in a field, it is preferable that all or the majority of the plants are at the same developmental stage. A particular herbicide or pesticide will have an optimal time for application. For example, a herbicide or pesticide may be best applied when the plant is at the 4-6 leaf stage. It is important that the vast majority of the plants in a field be at this stage when the grower applies the herbicide or pesticide. If the plants are too young, they may not be able to withstand the application dose. If the plants are too old, the dose may be too low. In addition, it is important that the vast majority of the plants mature at the same time because a grower will harvest all the plants at one time. These characteristics are not beneficial to wild type *Brassica* plants, and therefore are not found in nature. Similarly, a very high seed oil content in a *Brassica* plant is not necessarily beneficial to a wild-type seed, but is beneficial for man. These characteristics have been carefully bred into cultivated varieties and hybrids of *Brassica napus* by man for the benefit of man.

Plants that have been self-pollinated and selected for many generations become homozygous at almost all gene loci and produce a uniform population of true breeding progeny. A cross between two homozygous lines produces a uniform population of hybrid plants that may be heterozygous for many gene loci. A cross of two plants each heterozygous at a number of gene loci will produce a population of hybrid plants that differ genetically and will not be uniform.

The development of hybrids requires the development of homozygous inbred lines, the crossing of these lines and the evaluation of the crosses. Pedigree breeding and double haploidy are two breeding methods used to develop inbred lines from populations. Breeding programs combine desirable traits from two or more inbred lines or various broad-based sources into breeding pools from which new inbred lines are developed by self pollination and selection of desired phenotypes. The new inbreds are crossed with other inbred lines and the hybrids from these crosses are evaluated to determine those that have commercial potential.

Pedigree breeding starts with the crossing of two genotypes, each of which may have one or more desirable characteristics that are lacking in the other or which complement the other. If the two original parents do not provide all of the desired characteristics, other sources can be included in the breeding population. In the pedigree method, superior plants are self pollinated and their progenies are selected in successive generations. In the succeeding generations the heterozygous condition gives way to homogeneous lines as a result of self-pollination and selection. Typically in the pedigree method of breeding, five or more generations of self pollination and selection is practiced.

Double haploidy typically involves microspore isolation from a desired line. Once isolated, the microspores are cultured in vitro under specific culture conditions to induce embryogenesis. The resulting embryos develop into normal, but haploid plants. The embryos can either undergo spontaneous doubling of the chromosomes, or the chromosomes in the embryo cells can be induced to double by culturing the microspores, embryos, or resulting plants, in certain "chromosome doubling" agents, for example colchicine, and other agents as is known to those skilled in the art. Once the chromosomes have been doubled, the embryos or plants are referred to as doubled haploids. The doubled haploid plant will express all recessive genes and will be fully fertile. Because the recessive genes are expressed, doubled haploid plants are ideal candidates for genetic selection of recessive traits. The method of microspore culture and doubled haploid production is also a fast and efficient method to produce homozygous plants, which are homozygous at every locus. Accordingly, this method is ideal in the production of inbred lines. Methods of microspore culture and doubled haploid production in *Brassica* are well known to those skilled in the art. For example, see, Beversdorf, W. D., Charne D. G., Kott, L. S., Chuong, P. V., Polsoni, L. & Zilka, J. (1987) "The utilization of microspore culture and microspore-derived doubled-haploids in a rapeseed (*Brassica napus*) breeding program"—In Proc. 7th Int. Rapeseed Conf, (Organizing Committee, ed), pp. 13. Poznan, Poland; "Microspore Culture in *Brassica*", Swanson, Eric B., Chapter 17, p. 159 in Methods in Molecular Biology, vol. 6, *Plant Cell and Tissue Culture*, Ed. Jeffrey W.; "The Characterization of Herbicide Tolerant Plants in *Brassica napus* L. After In Vitro Selection of Microspores and Protoplasts" by Eric B. Swanson, et al., *Plant Cell Reports*, (1988) 7:83-87; "Microspore Mutagenesis and Selection: Canola Plants With Field Tolerance to the Imidazolinones", by Eric B. Swanson, et al., (1989) *Theor. Appl. Genetics* 78:525-530.

A hybrid is the cross of two inbred lines, each of which may have one or more desirable characteristics lacked by the other or which complement the other. The hybrid progeny of the first generation is designated $F_1$. In the development of hybrids, only the $F_1$ hybrid plants are sought. The $F_1$ hybrid is more vigorous than its inbred parents. This hybrid vigor, or heterosis, can be manifested in many ways, including increased vegetative growth and increased yield.

The development of a hybrid variety involves three steps: (1) the selection of superior plants from various germplasm pools; (2) the self pollination of the superior plants for several generations to produce a series of inbred lines, which although different from each other, each breed true and are highly uniform; and (3) crossing the selected inbred lines with unrelated inbred lines to produce the hybrid progeny ($F_1$). During the inbreeding process the vigor of the lines decreases. Vigor is restored when two unrelated inbred lines are crossed to produce the hybrid progeny ($F_1$). An important consequence of the homozygosity and homogeneity of the inbred lines is that the hybrid between any two inbreds will always be the same. Once the inbreds that give the best hybrids have been identified, the hybrid seed can be reproduced indefinitely as long as the homogeneity of the inbred parents is maintained.

A single cross hybrid is produced when two inbred lines are crossed to produce the F1 progeny. A double cross hybrid, is produced from four inbred lines crossed in pairs (A×B and C×D) and then the two $F_1$ hybrids are crossed again (A×B)× (C×D). Much of the hybrid vigor exhibited by $F_1$ hybrids is lost in the next generation ($F_2$). Consequently, seed from hybrid varieties is not used for planting stock. Likewise, it is very important in the production of hybrid seed to avoid harvesting self-pollinated seed from the inbreds and sale of inbred seed to end users.

The Ogura cytoplasmic male sterility and restorer system is used to form single cross *Brassica napus* F1 hybrids. Hybrid seed can be produced by planting parent plants as substantially homogeneous adjoining populations within pollination proximity in a planting area. Pollen from the male parent is transferred to the female parent to achieve fertilization of the female parent. F1 hybrid seeds are formed thereon.

Figure 2A:
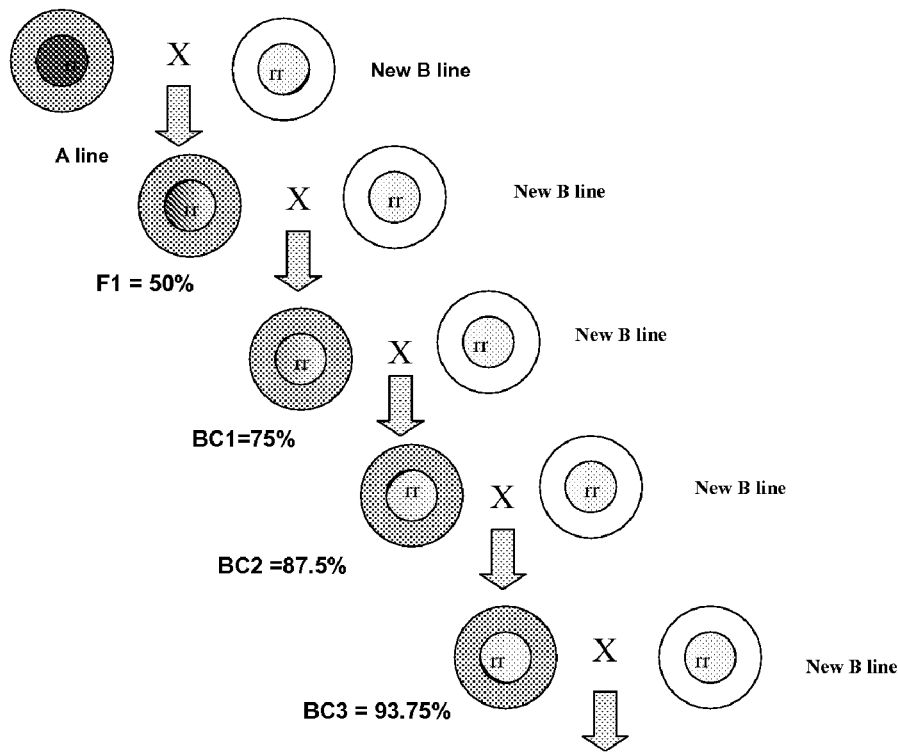
FIGS. 2*a* and 2*b*: Schematic showing ogu CMS line development and commercial seed production
Figure 2A:
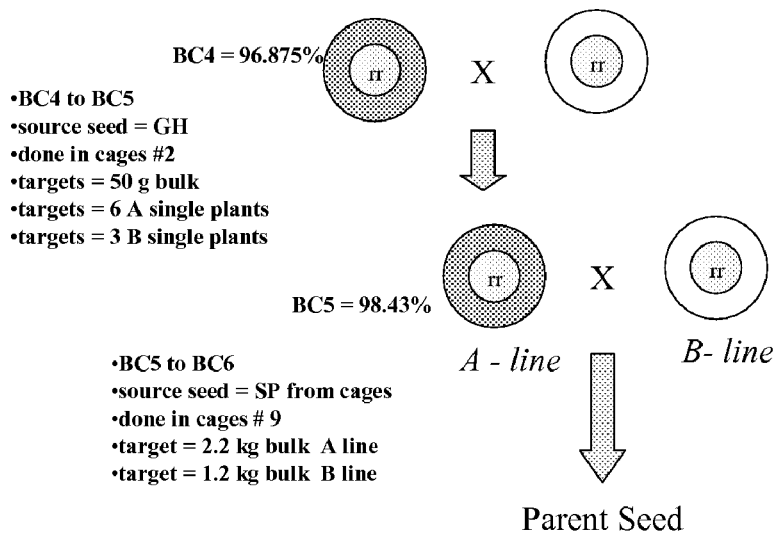
Figure 2B:
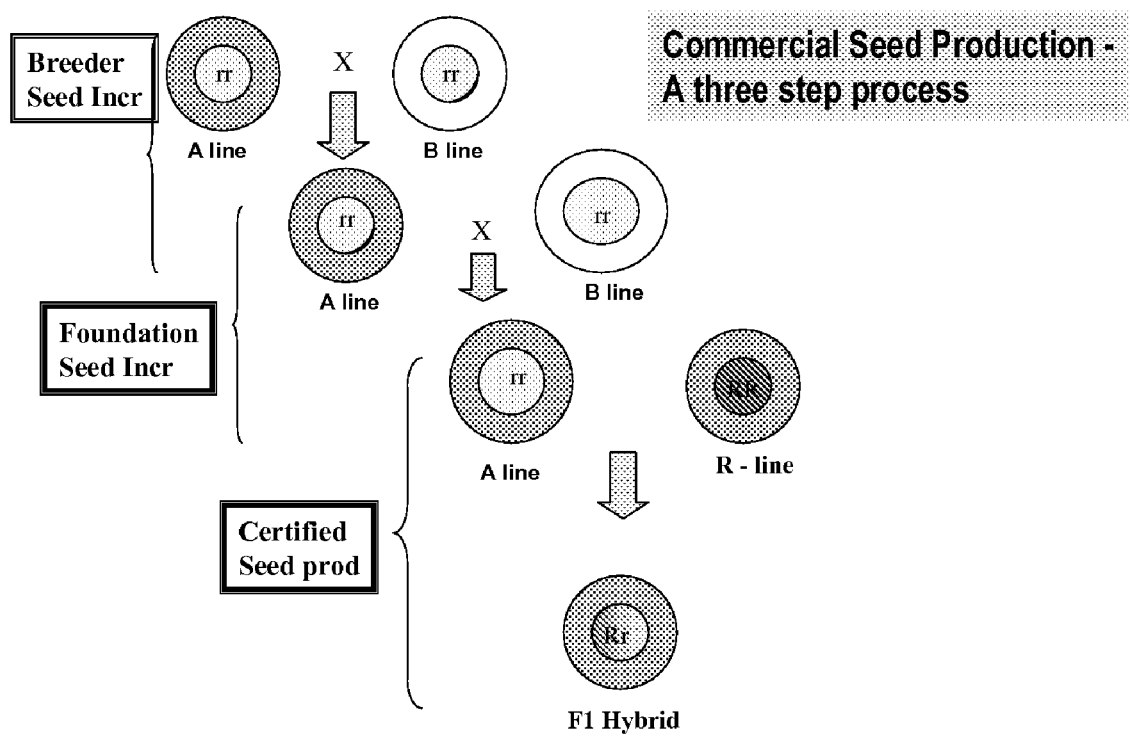

"Pollinating proximity" is used herein to specify that the parent plants are grown sufficiently close to make possible the transfer of pollen while maintaining the viability of such pollen. FIG. 2a and 2b are schematic diagrams which summarize the Ogura CMS system in Brassica.

The improved hybrid plant of the present invention is a product of the deliberate and meticulous breeding of specifically-defined Brassica napus inbred parent plants. Such parent plants have been tested through empirical research to be capable of yielding the advantageous results with respect to highly elevated oil content combined with good agronomic performance which commonly was lacking in the prior art.

The Brassica napus male sterile female parent (i.e., the seed parent) developed for use in the hybridization process of the present invention comprises an Ogura male sterile cytoplasm.

Because the Brassica napus female parent is male sterile, it cannot self propagate. In order to propagate and maintain the integrity of its genome it must be pollinated by an essentially isogenic Brassica napus line that lacks the Ogura male sterile cytoplasm. This line is commonly referred to as the maintainer line or B line.

The Brassica napus male parent (i.e., the pollen parent in the hybrid cross) selected for use in the hybridization process of the present invention possesses an Ogura restorer gene in the homozygous condition ($R_fR_f$). In this way each and every seed of the hybrid cross will possess one restorer gene and therefore, each and every seed will produce a plant which is fully male fertile. Accordingly, when the hybrid seed is planted in the grower's field, each and every hybrid plant can self pollinate and produce abundant yield for the grower.

The improved process of the present invention makes possible the formation of Brassica napus F1 hybrid seeds which when planted are capable of producing a crop that exceeds the yield of each parent used in the formation of the F1 hybrid (for example, the F1 hybrid would outyield the male parent and the female parent if each was grown in the same field at the same time and if each were self-pollinated, or in the case of the CMS female line, pollinated by a pollen source having substantially the same genotype as itself). In addition, the F1 hybrid seeds made possible by the use of the technology of the present invention commonly exhibit an oil content of approximately between 2.7% to 3.3% higher than current commercial checks. Brassica napus hybrid seeds designated 46P50 were deposited at the American Type Culture Collection, on Apr. 2, 2007. A 2,500 seed deposit of 46P50 has been assigned ATCC Accession No. PTA-8304.

It has been found that the combination of desired traits described herein once established can be transferred into other plants within Brassica napus and within other species of Brassica by conventional plant breeding techniques involving cross-pollination and selection of the progeny as is known to those skilled in the art. Accordingly, a descendent, a subline or a plant produced by crossing 46P50 with a second plant is also encompassed in this invention.

The improved oilseed Brassica hybrid plant of the present invention is capable of production in the field under conventional oilseed Brassica growing conditions that are commonly utilized during oilseed production on a commercial scale. Such oilseed Brassica exhibits good commercial agronomic characteristics and is capable upon self-pollination of forming oilseeds that possess the high oil trait.

The following Examples are presented as specific illustrations of the claimed invention. It should be understood, however, that the invention is not limited to the specific details set forth in the Examples.

EXAMPLES

Example 1

Development of Maintainer Line (B Line)

The maintainer—B line 98DHS-2554 was developed using double haploids from a three-way complex cross ((Quantum×NS2052)×46A65). The doubled haploids were produced as is known to those skilled in the art, and for example, as described in Fan, Z., Armstrong, K. C., Keller, W. A. (1988) Development of microspores in vivo and in vitro in Brassica napus L. Protoplasma 147:191-199; Beversdorf, W. D., Charne D. G., Kott, L. S., Chuong, P. V., Polsoni, L. & Zilka, J. (1987). The utilization of microspore culture and microspore-derived doubled-haploids in a rapeseed (Brassica napus) breeding program.—In Proc. 7th Int. Rapeseed Conf, (Organizing Committee, ed), pp. 13. Poznan, Poland; and Huang, B. (1992) Genetic manipulation of microspores and microspore-derived embryos. In Vitro Cell Dev. Biol. 28:53-58, to name a few. Quantum and 46A65 are registered as commercial varieties in Canada while NS2052 is a proprietary non-registered breeding line comprising a glyphosate resistance gene from the RT73 transgenic event. The RT73 transgenic event has regulatory approval in major export markets, for example the United States, Japan and Mexico. The last crossing was completed in 1996 and 142 doubled haploid (DHS) lines were extracted in 1997. The first 23 DHS lines with sufficient seed were evaluated in field nursery in 1998. The DHS lines were evaluated for glyphosate resistance, early maturity, lodging resistance, high oil and protein, agronomic score and uniformity. The remaining 119 DHS lines, that were not ready for the 1998 evaluation, were evaluated in 1999.

During the summer of 1999, these DHS lines were planted in a single replicate nursery experiment where every twentieth row was planted with a common check cultivar, 45A51. The rows were 2 metres in length. The experiment was planted at Georgetown, Ontario. During the growing season, observations were recorded on, days to flowering, and days to maturity, agronomic score at flowering and at maturity. At physiological maturity, lines were selected for general appearance and agronomic superiority based on breeder's observations. The selected lines were then analyzed for quality traits such as oil content, protein content, and total glucosinolates (adjusted to 8.5% moisture) using Near Infrared Analysis (NIR). Since every twentieth row was planted with a common check, 45A51, each selected line was compared to the mean of the common check rows of 45A51 occurring on both sides of the selected line. This comparison resulted in the calculation of deviations for oil, protein, and oil plus protein calculated for the respective trait from the mean of two common check (45A51) rows on both sides of selected rows. Since oil, protein and total glucosinolates values varied considerably for 45A51—the common check within the field, this method of adjustment made it possible to compare the oil and protein contents of all the selected DHS lines.

After reviewing the results of the quality and agronomic traits, a final list of lines was prepared. These lines were then evaluated in 2000 in an experiment planted at Georgetown, Ontario, using the same method of the 1999 nursery evaluation. The same common check 45A51 was used in 2000. After the evaluation of 2000, the list of selected DHS lines was shortened for 2001 evaluation.

The selected lines were evaluated in 2001 using the same experimental protocol as 1999 and 2000. After completing the 2001 nursery evaluation, a summary of quality traits as presented in Table 1 was tabulated. Based on three years of quality data, it was concluded that line 98DHS-2554 consistently exhibited high oil in three years of nursery experiments. Since the data summary was based on multiple years, there was reason to believe that high oil in 98DHS-2554 would be due to genetic factors rather than environmental factors alone. At the end of this evaluation, 98DHS-2554 was assigned a breeder code.

Example 2

Development of CMS Line Version of 98DHS-2554 (A Line)

After completion of the field nursery evaluation in 1999, several lines including 98DHS-2554 were selected to transfer to OGU (Ogura) cytoplasm by backcrossing. The objective was to convert 98DHS-2554 to a male sterile female line, so that it could be used in commercial hybrid production. The backcrossing was initiated in September of 1999. A breeding line carrying the OGU-INRA cytoplasm was used as a donor parent (female) and 98DHS-2554 was used as a recurrent parent (male—B line). The F1 was then used as a female and backcrossed to 98DHS-2554 to produce BC1 (see, FIG. 2a). The backcrossing was repeated six times under pollination controlled conditions. By the sixth backcross (seven doses of 98DHS-2554), 98DHS-2554 and resulting male sterile progenies (CMS version of 98DHS-2554) were genetically identical with the exception of the cytoplasm: 98DHS-2554 carried *Brassica napus* cytoplasm while 98DHS-2554-CMS carried the OGU-INRA cytoplasm. The OGU-INRA cytoplasm induces male sterility in 98DHS-2554-CMS. All the backcrossing generations from BC0 (F1) to BC5 were produced under controlled pollination conditions in the greenhouse, while BC6 was completed in a small cage (1.8 m×1.5 m) and BC7 was completed in a large cage (15 m×7.5 m) in the field. Breeder seed for this line was bulked at BC8.

Example 3

Development of Male Restorer Line 00SNR17250

00SNR17250 was developed from a bi-parental cross (NW1717M×46A65) that was completed in 1996. NW1717M is a winter canola proprietary and low glucosinolates restorer breeding line which comprises the OGU-INRA CMS cytoplasm. It was developed in Pioneer Hi-Bred's winter canola program in France. 46A65 is a commercial spring variety in Canada. The F1 plants were vernalized for 5-6 weeks, grown in the greenhouse and were harvested in bulk. The F2 plants were also grown in the greenhouse and fertile plants (25% of plants were CMS) were individually harvested to produce F3 lines. The F3 lines were further advanced to the F4 generation in the greenhouse during 1998. The F4 lines were then evaluated in 1999 in a single replicated nursery experiment planted at the research facility in Georgetown, Ontario. The experimental protocol was similar to what has been described above for the B line development except the common check used in this experiment was 46A65. The lines were selected for homozygosity of restorer gene, female fertility, general uniformity, early maturity and agronomic appearance. The selected lines were harvested and approximately 20 gram of bulk seed sample was collected from several random plants for quality analysis. Quality traits like oil, protein and total glucosinolates were analyzed using NIR.

The data from this trial is summarized in Table 2 which shows that line 99SNR11277, the F4 progenitor of 00SNR17250 expressed high levels of oil and had good protein and acceptable total glucosinolates. Also this F4 line was homozygous for the restorer gene, as all the plants within this line were fertile (scored as "F" as opposed to "S" for CMS segregation).

TABLE 1

Summary of oil, protein and total of oil plus protein expressed as percent deviation from common check 45A51. The total glucosinolates value is expressed in micromoles per gram of seed having moisture content of 8.5%.

| VARIETY | Oil Dev 3 Yr Avg | Oil Dev 1999 | Oil Dev 2000 | Oil Dev 2001 | Prot Dev 3 Yr Avg | Prot Dev 1999 | Prot Dev 2000 | Prot Dev 2001 | O + P Dev 3 Yr Avg | O + P Dev 1999 | O + P Dev 2000 | O + P Dev 2001 | Gluc @8.5 3 Yr Avg | Gluc @8.5 1999 | Gluc @8.5 2000 | Gluc @8.5 2001 |
|---|---|---|---|---|---|---|---|---|---|---|---|---|---|---|---|---|
| 98DHS-3018 | 0.0 | 0.0 | 1.7 | −1.7 | 3.1 | 1.7 | 5.9 | 1.7 | 3.1 | 1.6 | 7.6 | 0.0 | 8.9 | 8.4 | 7.8 | 10.7 |
| 98DHS-3338 | 0.2 | 1.5 | 0.1 | −1.0 | 0.0 | −0.7 | 1.4 | −0.6 | 0.3 | 0.8 | 1.8 | −1.6 | 9.9 | 9.2 | 8.2 | 12.4 |
| 98DHS-3351 | 0.5 | 1.1 | 0.7 | −0.4 | −0.6 | −0.5 | −0.3 | −0.9 | 0.0 | 0.6 | 0.7 | −1.3 | 8.1 | 10.5 | 4.8 | 9.1 |
| 98DHS-3380 | 0.2 | −0.1 | 1.0 | −0.4 | −0.5 | −0.7 | −1.6 | 0.7 | −0.3 | −0.8 | −0.3 | 0.3 | 10.9 | 11.2 | 7.5 | 14.0 |
| 98DHS-2981 | 0.1 | 0.3 | 0.1 | 0.1 | 2.0 | 0.6 | 3.2 | 2.3 | 2.1 | 0.9 | 3.2 | 2.3 | 10.1 | 9.1 | 8.2 | 13.0 |
| 98DHS-2959 | 0.8 | 0.8 | 1.0 | 0.7 | 0.6 | 0.1 | 1.6 | 0.2 | 1.4 | 0.9 | 2.5 | 0.9 | 11.9 | 12.2 | 7.8 | 15.6 |
| 98DHS-5678 | 0.9 | 1.5 | 0.6 | 0.7 | 0.0 | −0.8 | 0.7 | 0.0 | 0.9 | 0.6 | 1.4 | 0.8 | 10.0 | 10.7 | 7.8 | 11.4 |
| 98DHS-2409 | 1.8 | 0.3 | 4.1 | 1.0 | 2.1 | 1.8 | 2.8 | 1.9 | 3.9 | 2.0 | 6.9 | 2.9 | 13.9 | 14.0 | 10.8 | 16.8 |
| 98DHS-2886 | 1.7 | 2.8 | 1.3 | 1.1 | 1.0 | −0.9 | 3.1 | 0.8 | 2.7 | 2.0 | 4.3 | 1.9 | 11.1 | 12.1 | 6.5 | 14.6 |
| 98DHS-2626 | 2.5 | 3.2 | 2.9 | 1.4 | 3.3 | 0.3 | 5.2 | 4.3 | 5.8 | 3.4 | 8.1 | 5.7 | 7.2 | 4.0 | 6.6 | 11.1 |
| 98DHS-2955 | 0.1 | −0.3 | −0.8 | 1.5 | 1.2 | 0.8 | 2.6 | 0.2 | 1.3 | 0.5 | 1.7 | 1.7 | 7.5 | 6.7 | 6.1 | 9.9 |
| 98DHS-2609 | 2.1 | 0.9 | 3.5 | 1.9 | 0.2 | 0.4 | 1.2 | −0.8 | 2.4 | 1.3 | 4.8 | 1.1 | 6.3 | 7.1 | 4.4 | 7.5 |
| 98DHS-2401 | 1.3 | 0.4 | 1.6 | 2.0 | −0.4 | 0.1 | 0.0 | −1.4 | 0.9 | 0.5 | 1.5 | 0.6 | 12.1 | 13.0 | 9.4 | 13.8 |
| 98DHS-2554 | 3.2 | 3.2 | 4.2 | 2.4 | 0.7 | −1.4 | 3.5 | −0.1 | 3.9 | 1.8 | 7.7 | 2.3 | 11.6 | 10.5 | 10.8 | 13.4 |
| 98DHS-5600 | 2.3 | 1.0 | 3.5 | 2.4 | 0.4 | 0.4 | 0.6 | 0.4 | 2.7 | 1.4 | 4.1 | 2.8 | 9.3 | 9.5 | 6.7 | 11.8 |

TABLE 2

Summary of data for quality and agronomic traits for the lines selected from 1999 experiment where restorer lines were evaluated.

| VARIETY | Oil Dev | Prot Dev | O + P Dev | Gluc @ 8.5 H2O | Days To Flower | F/S | Days To Mat | Agscm* |
|---|---|---|---|---|---|---|---|---|
| 99SNR11255 | −1.5 | 2.1 | 0.5 | 14.1 | 53 | S | 92 | 7.5 |
| 99SNR11256 | 0.0 | 1.0 | 1.0 | 10.2 | 52 | S | 96 | 7.0 |
| 99SNR11263 | 5.3 | −2.0 | 3.2 | 9.7 | 48 | S | 94 | 7.5 |
| 99SNR11264 | 3.6 | −0.8 | 2.8 | 11.5 | 53 | S | 96 | 7.0 |
| 99SNR11265 | 2.8 | 0.1 | 2.9 | 7.6 | 53 | F | 97 | 7.5 |
| 99SNR11267 | 1.3 | 0.2 | 1.5 | 8.1 | 51 | S | 95 | 7.5 |
| 99SNR11268 | 1.5 | 0.3 | 1.8 | 11.1 | 52 | F | 97 | 7.5 |
| 99SNR11271 | 2.8 | −1.7 | 1.1 | 6.8 | 48 | S | 95 | 7.0 |
| 99SNR11276 | 3.1 | 0.3 | 3.3 | 7.7 | 55 | F | 102 | 6.5 |
| 99SNR11277 | 3.7 | −0.4 | 3.3 | 10.3 | 53 | F | 96 | 7.0 |
| 99SNR11278 | 2.6 | 0.2 | 2.8 | 6.0 | 52 | S | 95 | 6.5 |
| 99SNR11279 | 1.0 | 1.8 | 2.7 | 9.1 | 53 | F | 95 | 7.0 |
| 99SNR11280 | 1.8 | 0.5 | 2.3 | 10.3 | 52 | S | 97 | 7.0 |
| 99SNR11289 | 0.3 | 1.9 | 2.2 | 17.6 | 49 | S | 98 | 6.5 |
| 99SNR11290 | 2.6 | −1.2 | 1.4 | 12.6 | 47 | S | 94 | 7.0 |
| 99SNR11300 | 3.6 | −3.2 | 0.5 | 6.3 | 50 | F | 92 | 6.5 |
| 99SNR11318 | −0.5 | 0.9 | 0.4 | 12.8 | 55 | S | 100 | 7.0 |
| 99SNR11324 | 0.6 | −1.1 | −0.5 | 13.9 | 51 | S | 101 | 7.5 |
| 99SNR11345 | 1.9 | −0.7 | 1.1 | 16.4 | 53 | F | 97 | 7.0 |
| 99SNR11347 | 1.4 | −0.8 | 0.7 | 20.5 | 53 | F | 100 | 7.5 |
| 99SNR11348 | 2.3 | −0.3 | 2.1 | 8.4 | 48 | F | 97 | 7.0 |
| 99SNR11349 | 0.8 | 0.8 | 1.5 | 6.5 | 48 | F | 98 | 8.0 |
| 99SNR11360 | 1.2 | −2.1 | −0.8 | 8.9 | 51 | S | 97 | 7.0 |
| 99SNR11366 | 1.8 | −2.2 | −0.4 | 9.1 | 54 | S | 98 | 6.5 |
| 99SNR11376 | −1.6 | 3.2 | 1.6 | 7.4 | 51 | F | 95 | 7.5 |
| 99SNR11378 | −0.9 | 2.0 | 1.1 | 13.3 | 54 | F | 98 | 7.0 |
| 99SNR11379 | 0.4 | −0.5 | −0.1 | 10.9 | 48 | F | 94 | 7.0 |
| 99SNR11382 | 0.4 | 0.5 | 1.0 | 13.3 | 53 | F | 95 | 7.5 |
| 99SNR11388 | 0.5 | 0.3 | 0.8 | 10.3 | 52 | F | 99 | 6.5 |
| 99SNR11395 | −1.5 | 0.4 | −1.1 | 9.5 | 49 | S | 93 | 7.0 |
| 99SNR11397 | 1.2 | −2.0 | −0.8 | 10.5 | 48 | S | 94 | 7.5 |

*agscm refers to agronomic score at maturity

Self pollinated seed from the selected line produced the F5 generation and was assigned a new number 00SNR04038. The F5 line 00SNR04038 was sent to Chile during the fall of 1999 and was evaluated in the Chile nursery along with several other homozygous restorer lines in a single replicate experiment as described above. At flowering, random flowers from each line were collected and were used for pollinating two female CMS lines: CMS line 1 and CMS line 2. This method of crossing produced two hybrids (testcrosses) for each male line. Also, each male line was self-pollinated to produce F6 seed. The open pollinated seed samples were collected from each selected restorer line from Chile and were analyzed for quality parameters such as oil and protein content and total glucosinolates using the NIR method. The results of the analysis for F5 00SNR04038 are presented in Table 3.

The F6 seed and corresponding two testcrosses were evaluated in a single replicated nursery experiment planted during the summer of 2000 in Ontario. The nursery experimental protocol and recording of observations were as described above including the planting of common check, 46A65.

The results of quality analysis of line 00SNR17250 were inconclusive as far as high oil was concerned. As presented in Table 3, line 00SNR17250 exhibited—0.4% oil deviation, although both the testcrosses showed high oil. The previous generations of 00SNR17250 (F5 and F4) showed considerable high oil. This type of inconsistency can occur in a single replicated nursery experiment if the environmental variation is higher than the genetic variation.

Male line 00SNR17250 was considered a finished line and a breeder code was assigned to this line. This line was sent to Chile for hybrid seed production involving six females (testers).

Example 4

Combining Ability Evaluation of Inbred Lines 4.1. Combining Ability Evaluation of Male Inbred: 00SNR17250

Male inbred line 00SNR17250 was crossed to the CMS version of six B lines. These six lines (94SN-3253, 94SN-

TABLE 3

Quality data summary of F5 and F6 lines and testcrosses produced using F5 pollen.

| Generation | Line number | Test location | Oil Dev | Prot Dev | O + P Dev | Gluc @ 8.5 Dev | Segregation Score |
|---|---|---|---|---|---|---|---|
| F5 | 00SNR04038 | Chile 1999-2000 | 1.3 | 0.5 | 1.8 | 17.0 | F |
| F6 | 00SNR17250 | Ontario 2000 | −0.4 | 3.2 | 2.8 | 14.6 | F |
| Testcross 1 | CMS line 1 × 00SNR17250 | Ontario 2000 | 3.0 | −3.1 | −0.1 | 10.2 | F |
| Testcross 2 | CMS line 2 × 00SNR17250 | Ontario 2000 | 3.9 | −3.5 | 0.4 | 11.8 | F |

3252, 97DHS-2044, 96DHS-60, 95SN-5482, and 96DHS-22) were identified as high combining lines from previous experiments. They all received a breeder code, were converted to CMS females, and were considered testers. The male×female tester based hybrid performance data as collected from 2001 first year single replicate trials over five locations is presented in Table 4. The average performance of each male over six females, including 00SNR17250, is presented as half-sib mean for various traits. Several experiments were conducted, each including hybrids based on 4 new males×6 female testers (24 hybrids in each trial). The half-sib mean represents general combining ability (GCA) of the inbred line. Based on 2001 GCA data, 00SNR17250 showed favourable GCA (half-sib mean) for yield, oil % and total saturated fats. This restorer line was selected for further evaluation the following year.

In 2002, several of the selected male lines from the 2001 first year experiments were evaluated in the second year trials replicated twice, over three locations. The hybrid data, based on four males (including 00SNR17250) by five of the same six females evaluated in the 2002 experiments, is presented in Table 5. Male inbred 00SNR17250 showed favourable GCA for yield, oil % and total saturates. The results of this experiment were consistent with the results observed in 2001. Therefore, after the 2002 evaluation, the male line 00SNR17250 was designated as a male tester for hybrid production and used for the evaluation of GCA of other new female lines.

4.2 Combining Ability Evaluation of Female Inbred: 98DHS-2554-CMS

The female line 98DHS-2554-CMS was crossed to six restorer lines (00SNR05154, 00SNR05171, 01SNR07779, 01SNR08006, 01SNR08170 and 01SNR08241). These six restorer lines were identified as high combining lines from previous experiments. They all received breeder code and were considered testers. The new female×male tester based hybrid performance data, collected from 2002 single replicated first year trials over three locations is presented in Table 6. The average performance of each female over six males, including 98DHS-2554, is presented as half-sib mean for various traits. The half-sib mean represents the general combining ability of the inbred line. During the 2002 season, several field trials were conducted, each included hybrids based on four new females×six male testers. Based on the 2002 first year data, the 98DHS-2554 line showed favorable GCA for yield and oil traits. It was selected and advanced to the next level.

Example 5

Development and Evaluation of Hybrid 46P50 (03N322R)

5.1 Development and Evaluation of Hybrid 46P50 in 2003 second year trials:

During 2003, female line 98DHS-2554-CMS was advanced to the next level and male line 00SNR17250 was designated as a tester male. The hybrid between these two parental lines was not produced before 2003. During the fall of 2002 and winter of 2003, the new hybrid between 98DHS-2554-CMS×00SNR17250 was produced in Chile and was assigned a breeder code "03N322R". Hybrid 03N322R was tested in two replicated second year trials over six locations in 2003.

The results are summarized in Table 7 which shows that the hybrid 03N322R yielded 118% of 46A65 and Q2 (registration checks) and 100% of commercial hybrid checks (45H21 and InVigor 2663). For other traits such as days to maturity, plant height, oil %, protein %, and total glucosinolates, the value for each hybrid in Table 7 is expressed as deviation from the mean of 46A65 and Q2 for the trait in question. In this way, all the hybrids from the various trials can be compared. For blackleg disease (BL 1-9), the values are expressed on 1 to 9 score where 1=very poor and 9=best. The percent oil was calculated as 2.3% greater than the average of 46A65 and Q2. Based on 2003 data, hybrid 03N322 was selected for further testing together with some other hybrids presented in Table 7.

TABLE 4

Hybrid performance data based on new males × female testers for various traits
(data source 2001 first year trials)

| Female | 00SNR14499 | 00SNR14503 | 00SNR14519 | 00SNR17250 | Half-sib mean |
|---|---|---|---|---|---|
| Yield % of 46A65 and Q2 | | | | | |
| 94SN-3253 | 109.0 | 109.0 | 115.0 | 126.0 | 114.8 |
| 94SN-3252 | 108.0 | 140.0 | 124.0 | 126.0 | 124.5 |
| 97DHS-2044 | 129.0 | 140.0 | 150.0 | 135.0 | 138.5 |
| 96DHS-60 | 106.0 | 122.0 | 118.0 | 124.0 | 117.5 |
| 95-SN-5482 | 115.0 | 130.0 | 109.0 | 134.0 | 122.0 |
| 96DHS-22 | 96.0 | 108.0 | 119.0 | 108.0 | 107.8 |
| Half-sib mean | 110.5 | 124.8 | 122.5 | 125.5 | 120.8 |
| Days to Maturity | | | | | |
| 94SN-3253 | 95.5 | 96.3 | 98.0 | 98.3 | 97.0 |
| 94SN-3252 | 95.0 | 96.3 | 96.0 | 96.0 | 95.8 |
| 97DHS-2044 | 95.8 | 96.3 | 97.0 | 96.5 | 96.4 |
| 96DHS-60 | 94.8 | 95.3 | 94.8 | 96.0 | 95.2 |
| 95-SN-5482 | 95.8 | 95.3 | 96.3 | 98.0 | 96.4 |
| 96DHS-22 | 93.8 | 94.8 | 96.0 | 95.5 | 95.0 |
| Half-sib mean | 95.1 | 95.7 | 96.4 | 96.7 | 96.0 |
| Plant height (cm) | | | | | |
| 94SN-3253 | 97.5 | 112.5 | 120.0 | 110.0 | 110.0 |
| 94SN-3252 | 100.0 | 110.0 | 107.5 | 107.5 | 106.3 |
| 97DHS-2044 | 110.0 | 110.0 | 107.5 | 112.5 | 110.0 |
| 96DHS-60 | 97.5 | 110.0 | 130.0 | 105.0 | 110.6 |

TABLE 4-continued

Hybrid performance data based on new males × female testers for various traits
(data source 2001 first year trials)

| Female | 00SNR14499 | 00SNR14503 | 00SNR14519 | 00SNR17250 | Half-sib mean |
|---|---|---|---|---|---|
| 95-SN-5482 | 95.0 | 115.0 | 110.0 | 100.0 | 105.0 |
| 96DHS-22 | 105.0 | 97.5 | 117.5 | 112.5 | 108.1 |
| Half-sib mean | 100.8 | 109.2 | 115.4 | 107.9 | 108.3 |
| Oil % | | | | | |
| 94SN-3253 | 44.9 | 45.0 | 45.3 | 46.0 | 45.3 |
| 94SN-3252 | 45.2 | 44.3 | 45.9 | 46.4 | 45.4 |
| 97DHS-2044 | 43.4 | 44.3 | 45.0 | 45.9 | 44.7 |
| 96DHS-60 | 44.0 | 44.2 | 43.4 | 45.7 | 44.3 |
| 95-SN-5482 | 44.0 | 44.5 | 43.4 | 45.0 | 44.2 |
| 96DHS-22 | 44.5 | 45.0 | 44.4 | 46.0 | 45.0 |
| Half-sib mean | 44.3 | 44.6 | 44.5 | 45.8 | 44.8 |
| Total Glucosinolates (umol/g) @ 8.5% moisture | | | | | |
| 94SN-3253 | 13.5 | 14.1 | 14.8 | 16.3 | 14.7 |
| 94SN-3252 | 13.6 | 15.8 | 13.1 | 14.3 | 14.2 |
| 97DHS-2044 | 14.8 | 15.8 | 17.0 | 17.7 | 16.3 |
| 96DHS-60 | 11.8 | 12.8 | 13.4 | 14.2 | 13.0 |
| 95-SN-5482 | 12.9 | 12.8 | 13.3 | 14.6 | 13.4 |
| 96DHS-22 | 13.1 | 12.4 | 13.8 | 14.6 | 13.5 |
| Half-sib mean | 13.3 | 13.9 | 14.2 | 15.3 | 14.2 |
| Total Saturates % | | | | | |
| NS2173FC | 8.6 | 6.3 | 6.3 | 6.1 | 6.8 |
| NS2082FC | 6.2 | 6.4 | 6.3 | 6.1 | 6.2 |
| NS03213FI | 6.3 | 6.4 | 6.3 | 6.0 | 6.2 |
| NS2634FR | 6.4 | 6.4 | 6.6 | 6.3 | 6.4 |
| NS2335FR | 6.5 | 6.3 | 6.8 | 6.4 | 6.5 |
| NS2627FR | 6.3 | 6.6 | 6.5 | 6.3 | 6.4 |
| Half-sib mean | 6.7 | 6.4 | 6.5 | 6.2 | 6.4 |

TABLE 5

Hybrid performance data based on new males × female testers for various traits
(data source 2002 first year trials)

| Female | 00SNR14471 | 00SNR14503 | 00SNR17250 | 00SNR5171 | Half-sib mean |
|---|---|---|---|---|---|
| Yield % 46A65 and Q2 | | | | | |
| 94SN-3252 | 109.0 | 106.0 | 110.0 | 106.0 | 107.8 |
| 94SN-3253 | 119.0 | 109.0 | 112.0 | 114.0 | 113.5 |
| 95-SN-5482 | 117.0 | 107.0 | 109.0 | 108.0 | 110.3 |
| 96DHS-22 | 110.0 | 96.0 | 114.0 | 113.0 | 108.3 |
| 96DHS-60 | 117.0 | 114.0 | 114.0 | 113.0 | 114.5 |
| Half-sib mean | 114.4 | 106.4 | 111.8 | 110.8 | 110.9 |
| Days to Maturity | | | | | |
| 94SN-3252 | 96.2 | 96.2 | 96.0 | 96.0 | 96.1 |
| 94SN-3253 | 96.5 | 97.2 | 96.2 | 96.2 | 96.5 |
| 95-SN-5482 | 97.3 | 96.0 | 96.7 | 96.0 | 96.5 |
| 96DHS-22 | 94.2 | 95.0 | 94.5 | 94.0 | 94.4 |
| 96DHS-60 | 94.8 | 94.3 | 95.7 | 94.0 | 94.7 |
| Half-sib mean | 95.8 | 95.7 | 95.8 | 95.2 | 95.7 |
| Plant height (cm) | | | | | |
| 94SN-3252 | 91.2 | 87.5 | 95.7 | 85.2 | 89.9 |
| 94SN-3253 | 105.0 | 92.8 | 104.7 | 94.2 | 99.2 |
| 95-SN-5482 | 97.3 | 90.7 | 100.0 | 93.3 | 95.3 |
| 96DHS-22 | 90.7 | 91.2 | 96.7 | 90.0 | 92.2 |
| 96DHS-60 | 98.7 | 90.7 | 109.0 | 98.3 | 99.2 |
| Half-sib mean | 96.6 | 90.6 | 101.2 | 92.2 | 95.1 |
| Oil % | | | | | |
| 94SN-3252 | 49.1 | 48.1 | 50.4 | 48.2 | 49.0 |
| 94SN-3253 | 49.6 | 47.1 | 50.7 | 47.7 | 48.8 |
| 95-SN-5482 | 46.7 | 45.8 | 48.8 | 46.6 | 47.0 |
| 96DHS-22 | 47.6 | 47.5 | 49.4 | 47.9 | 48.1 |
| 96DHS-60 | 47.7 | 46.2 | 50.5 | 47.3 | 47.9 |
| Half-sib mean | 48.1 | 46.9 | 49.9 | 47.5 | 48.1 |

TABLE 5-continued

Hybrid performance data based on new males × female testers for various traits
(data source 2002 first year trials)

| Female | 00SNR14471 | 00SNR14503 | 00SNR17250 | 00SNR5171 | Half-sib mean |
|---|---|---|---|---|---|
| Total Glucosinolates | | | | | |
| 94SN-3252 | 15.6 | 16.2 | 15.0 | 16.7 | 15.9 |
| 94SN-3253 | 16.3 | 18.0 | 14.8 | 17.4 | 16.6 |
| 95-SN-5482 | 14.9 | 16.0 | 14.6 | 16.8 | 15.6 |
| 96DHS-22 | 14.6 | 12.6 | 12.8 | 14.1 | 13.5 |
| 96DHS-60 | 13.0 | 15.6 | 13.0 | 13.7 | 13.8 |
| Half-sib mean | 14.9 | 15.7 | 14.0 | 15.7 | 15.1 |
| Total Saturates | | | | | |
| 94SN-3252 | 6.2 | 6.4 | 6.1 | 6.4 | 6.3 |
| 94SN-3253 | 6.1 | 6.3 | 6.2 | 6.4 | 6.2 |
| 95-SN-5482 | 6.5 | 6.7 | 6.3 | 6.4 | 6.5 |
| 96DHS-22 | 6.5 | 6.7 | 6.4 | 6.5 | 6.5 |
| 96DHS-60 | 6.6 | 6.7 | 6.3 | 6.6 | 6.5 |
| Half-sib mean | 6.4 | 6.6 | 6.3 | 6.5 | 6.4 |

TABLE 6

Hybrid performance data based on new females × male testers for various traits
(data source 2002 first year trials)

| Female | 00SNR05154 | 00SNR5171 | 01SNR07779 | 01SNR08006 | 01SNR08170 | 01SNR08241 | Half-sib mean |
|---|---|---|---|---|---|---|---|
| Yield % of 46A65 and Q2 | | | | | | | |
| 98DHS-2401 | 112.0 | 104.0 | 104.0 | 114.0 | 104.0 | 94.0 | 105.3 |
| 98DHS-2554 | 129.0 | 103.0 | 109.0 | 121.0 | 122.0 | 116.0 | 116.7 |
| 98DHS-2609 | 120.0 | 100.0 | 97.0 | 97.0 | 102.0 | 112.0 | 104.7 |
| 98DHS-2626 | 126.0 | 120.0 | 119.0 | 114.0 | 101.0 | 101.0 | 113.5 |
| Half-sib mean | 121.8 | 106.8 | 107.3 | 111.5 | 107.3 | 105.8 | 110.0 |
| Days to Maturity | | | | | | | |
| 98DHS-2401 | 96.3 | 93.7 | 98.0 | 94.7 | 96.0 | 96.3 | 95.8 |
| 98DHS-2554 | 97.7 | 94.7 | 98.0 | 95.3 | 98.7 | 94.3 | 96.5 |
| 98DHS-2609 | 98.0 | 94.0 | 95.3 | 94.3 | 95.0 | 94.3 | 95.2 |
| 98DHS-2626 | 96.7 | 94.7 | 97.7 | 95.3 | 95.3 | 94.3 | 95.7 |
| Half-sib mean | 97.2 | 94.3 | 97.3 | 94.9 | 96.3 | 94.8 | 95.8 |
| Plant height (cm) | | | | | | | |
| 98DHS-2401 | 94.7 | 92.3 | 93.3 | 98.3 | 92.0 | 93.3 | 94.0 |
| 98DHS-2554 | 102.0 | 91.7 | 102.0 | 92.0 | 95.0 | 97.3 | 96.7 |
| 98DHS-2609 | 97.3 | 90.7 | 99.3 | 89.0 | 96.3 | 92.3 | 94.2 |
| 98DHS-2626 | 101.7 | 92.0 | 97.0 | 89.0 | 95.0 | 88.7 | 93.9 |
| Half-sib mean | 98.9 | 91.7 | 97.9 | 92.1 | 94.6 | 92.9 | 94.7 |
| Oil % | | | | | | | |
| 98DHS-2401 | 47.2 | 47.3 | 47.9 | 47.5 | 48.6 | 48.8 | 47.9 |
| 98DHS-2554 | 48.2 | 47.8 | 48.6 | 48.1 | 49.3 | 47.6 | 48.2 |
| 98DHS-2609 | 46.3 | 45.5 | 47.9 | 46.2 | 48.0 | 47.5 | 46.9 |
| 98DHS-2626 | 47.3 | 47.2 | 48.1 | 47.3 | 48.3 | 47.2 | 47.6 |
| Half-sib mean | 47.3 | 46.9 | 48.1 | 47.3 | 48.5 | 47.8 | 47.6 |
| Total Glucosinolates umol/g (8.5% moisture) | | | | | | | |
| 98DHS-2401 | 17.2 | 14.4 | 14.1 | 13.3 | 12.5 | 10.9 | 13.7 |
| 98DHS-2554 | 14.4 | 13.9 | 13.6 | 13.2 | 11.8 | 12.9 | 13.3 |
| 98DHS-2609 | 15.2 | 16.6 | 15.0 | 15.4 | 12.7 | 13.4 | 14.7 |
| 98DHS-2626 | 15.8 | 12.7 | 12.3 | 12.9 | 11.9 | 12.3 | 13.0 |
| Half-sib mean | 15.7 | 14.4 | 13.8 | 13.7 | 12.2 | 12.4 | 13.7 |
| Total Saturates % | | | | | | | |
| 98DHS-2401 | 6.1 | 6.0 | 5.8 | 6.1 | 6.1 | 6.1 | 6.0 |
| 98DHS-2554 | 6.1 | 6.4 | 6.1 | 6.1 | 6.1 | 6.1 | 6.1 |
| 98DHS-2609 | 6.2 | 6.2 | 6.1 | 6.4 | 5.9 | 5.8 | 6.1 |
| 98DHS-2626 | 6.2 | 6.1 | 6.0 | 6.1 | 6.3 | 6.0 | 6.1 |
| Half-sib mean | 6.1 | 6.2 | 6.0 | 6.2 | 6.1 | 6.0 | 6.1 |

TABLE 7

Data summary of hybrids tested in 2003 trails.

| Test | Variety | Yield % 46A65 & Q2 | Yield % Hybrid checks | Days to mat (dev) | Plant Ht cm (dev) | Oil % (dev) | Prot (dev) | Total Gluc (dev) | Total Sat % (dev) | BL 1-9 1 = poor 9 = best |
|---|---|---|---|---|---|---|---|---|---|---|
| Exp 2 | 03N324R | 119 | 100 | −0.2 | 0.5 | 2.2 | 2.0 | −5.1 | 0.0 | 8.0 |
| Exp 2 | 03N231R | 118 | 100 | −0.8 | 4.6 | 0.2 | 1.4 | −2.3 | 0.2 | 7.9 |
| Exp 2 | 03N230R | 118 | 100 | −1.3 | 5.2 | 0.7 | −0.7 | −3.2 | 0.2 | 8.2 |
| Exp 2 | 03N322R | 118 | 100 | 0.9 | 11.9 | 2.3 | 0.8 | −1.3 | −0.2 | 8.4 |
| Exp 2 | 03N232R | 116 | 98 | −2.9 | −5.3 | 0.9 | 0.3 | −4.5 | 0.1 | 7.5 |
| Exp 2 | 03N242R | 116 | 98 | −2.1 | −5.5 | 1.8 | 1.7 | −6.0 | 0.0 | 8.0 |
| Exp 2 | 03N217R | 120 | 101 | −0.4 | −2.2 | 0.1 | 3.8 | −2.9 | 0.1 | 7.5 |
| Exp 2 | 03N298R | 118 | 100 | −0.9 | 7.3 | 1.5 | 0.3 | 0.9 | 0.0 | 7.5 |
| Exp 2 | 03N300R | 120 | 102 | −1.5 | 1.6 | 0.6 | 2.0 | −3.4 | 0.1 | 7.2 |
| Exp 3 | 03N326R | 130 | 106 | −1.3 | 5.8 | 2.3 | 0.7 | −4.4 | −0.2 | 8.0 |
| Exp 3 | 03N234R | 129 | 106 | −3.8 | 5.6 | 0.9 | −0.3 | −4.6 | 0.1 | 8.0 |
| Exp 3 | 03N327R | 129 | 106 | −0.1 | 3.0 | 2.1 | 0.3 | −2.8 | −0.4 | 7.9 |
| Exp 4 | 03N236R | 122 | 98 | −1.5 | 1.2 | 0.2 | 0.3 | −2.0 | 0.0 | 7.2 |
| Exp 4 | 03N247R | 120 | 97 | −2.9 | −1.5 | 1.9 | 2.4 | −3.2 | 0.0 | 7.1 |
| Exp 4 | 03N329R | 120 | 96 | 0.5 | 7.3 | 2.7 | 2.9 | −2.8 | −0.1 | 7.9 |
| Exp 5 | 03N310R | 122 | 98 | 1.0 | 11.9 | 2.1 | 1.4 | −2.3 | −0.1 | 7.9 |
| Exp 6 | 03N317R | 126 | 106 | 0.8 | 12.2 | 1.5 | 1.8 | −5.0 | −0.1 | 7.7 |
| Exp 6 | 03N313R | 125 | 106 | 0.5 | 15.3 | 1.5 | 0.4 | −1.4 | −0.3 | 8.3 |
| Exp 6 | 03N319R | 121 | 103 | 1.8 | 11.1 | 2.0 | 2.5 | −0.9 | −0.3 | 7.8 |
| Exp 7 | 03N370R | 122 | 101 | −0.2 | 12.8 | 3.5 | 3.1 | −4.6 | −0.2 | 7.8 |
| Exp 8 | 03N393R | 127 | 101 | −2.0 | 8.6 | 3.3 | −1.1 | −6.4 | −0.1 | 7.8 |

5.2 Evaluation of Hybrid 03N322R in Advanced Trials in 2004 and 2005.

In 2004, hybrid 03N322R was tested in four replicated advanced (private co-op) trials planted at 23 locations. The data collected from this trial for various traits is presented in Table 8. Yield is expressed as percentage of 46A65 and Q2 and hybrid checks (45H21 and InVigor 5070) are presented respectively in the second and the third column in Table 8. For the other traits such as days to maturity, plant height, oil %, protein %, total glucosinolates expressed in micromoles per gram of seed at 8.5% moisture, chlorophyll (ppm) and total saturated fatty acids, observations are presented as the deviation from the mean of 46A65 and Q2—both being the registration checks. Blackleg data is presented as absolute score from 1=poor to 9=best. Hybrid 03N322R exhibited high yield and blackleg tolerance, acceptable plant height, maturity, glucosinolates and chlorophyll and showed very high oil and low total saturated fatty acids.

The percent oil of 03N322R was 3.5% higher than the average of 46A65 and Q2. After reviewing this data, it was decided to advance 03N322R into 2005 Public Co-op trials.

TABLE 8

Data summary of 2004 advanced trials involving 03N322R (46P50)

| VARIETY | YIELD % 46A65 & Q2 | Yield % hybrid chk | Mat Dev | Plant Height Dev | Oil % Dev | Protein % Dev | Total Gluc @ 8.5% H2O Dev | Chlorophyll ppm Dev | Total Sat % Dev | BL (1-9) 1 = poor, 9 = best |
|---|---|---|---|---|---|---|---|---|---|---|
| 03N298R | 122 | 106 | −1.0 | 3.5 | 3.2 | 0.7 | −1.5 | 0.8 | −0.2 | 7.5 |
| 03N230R | 122 | 105 | −2.1 | −1.5 | 1.7 | −0.2 | −1.4 | −3.4 | 0.1 | 8.1 |
| 03N322R | 121 | 105 | 1.7 | 3.5 | 3.5 | 0.7 | −2.4 | −0.2 | −0.3 | 7.9 |
| 03N234R | 121 | 104 | −3.3 | −3.5 | 0.6 | 0.9 | −2.6 | −5.4 | 0.0 | 7.8 |
| 03N317R | 120 | 103 | 0.1 | 5.5 | 1.2 | 0.8 | −4.9 | 4.6 | −0.1 | 7.4 |
| 03N231R | 120 | 103 | −2.6 | −4.5 | 0.8 | 1.3 | −0.6 | −8.7 | 0.1 | 7.6 |
| 03N313R | 119 | 102 | 0.9 | 11.5 | 2.5 | −0.7 | −3.9 | −6.3 | −0.3 | 7.1 |
| 03N327R | 119 | 102 | −0.8 | −0.5 | 1.2 | 0.8 | −2.8 | −7.4 | −0.3 | 7.4 |
| 03N236R | 118 | 102 | −2.1 | −1.5 | 0.4 | 0.6 | −1.4 | −4.6 | −0.1 | 7.6 |
| 03N217R | 117 | 100 | −2.9 | −4.5 | 0.3 | 2.3 | −2.1 | −6.3 | 0.1 | 7.9 |
| 03N393R | 116 | 100 | −0.8 | 3.5 | 1.3 | 0.0 | −3.9 | 1.1 | 0.0 | 8 |
| 03N326R | 115 | 99 | −1.1 | 1.5 | 1.6 | 1.3 | −3.0 | −0.8 | −0.1 | 8.2 |
| 03N324R | 115 | 98 | −1.1 | −3.5 | 2.0 | 1.6 | −3.5 | −1.9 | −0.2 | 7.8 |
| 03N232R | 115 | 98 | −3.8 | −8.5 | 0.8 | 0.9 | −2.9 | −8.9 | 0.1 | 7.9 |
| 03N310R | 114 | 97 | −0.3 | 4.5 | 2.1 | 0.9 | −1.8 | −1.2 | −0.2 | 7.9 |
| 03N370R | 112 | 96 | −0.5 | 3.5 | 3.8 | 2.1 | −3.5 | 1.4 | −0.3 | 7.6 |
| 03N329R | 110 | 96 | 1.1 | 0.5 | 2.7 | 1.9 | −3.1 | −1.4 | −0.5 | 7.8 |
| 03N247R | 109 | 94 | −2.9 | −5.5 | 2.2 | 2.2 | −2.9 | −8.0 | −0.3 | 7.3 |
| 03N319R | 109 | 94 | 1.6 | 3.5 | 1.7 | 1.6 | −3.3 | −1.2 | −0.1 | 7.6 |
| 03N300R | 109 | 93 | −2.7 | −4.5 | 0.8 | 1.3 | −2.5 | −5.2 | 0.0 | 7.4 |

TABLE 8-continued

Data summary of 2004 advanced trials involving 03N322R (46P50)

| VARIETY | YIELD % 46A65 & Q2 | Yield % hybrid chk | Mat Dev | Plant Height Dev | Oil % Dev | Protein % Dev | Total Gluc @ 8.5% H2O Dev | Chlorophyll ppm Dev | Total Sat % Dev | BL (1-9) 1 = poor, 9 = best |
|---|---|---|---|---|---|---|---|---|---|---|
| 03N242R | 109 | 92 | −4.6 | −7.5 | 2.0 | 1.5 | −3.7 | −5.2 | −0.3 | 7.2 |
| No of loc | 23 | 23 | 17 | 13 | 22 | 22 | 22 | 22 | 22 | 3 |

In 2005, 03N322 was also planted in Pioneer Hi-Bred's advanced trials at 22 locations of which only 17 locations produced acceptable data. All the data from 2003, 2004 and 2005 were subsequently pooled in order to create a pair wise comparison of 03N322R to three checks 46A65, Q2 and 45H21 (Table 9). 03N322 exhibited higher yield than 46A65, Q2 and also 45H21. It also consistently out performed these checks at a majority of sites and exhibited higher oil, protein, lower total saturates and better blackleg tolerance. For example on average, 03N322 produced 3.2% more oil than 46A65, 3.0% more oil than Q2 and 3.3% more oil than 45H21 over at least 48 locations. The percentage oil in the seed ranged from 51.4 to 51.8% across all years as measured at 0% moisture.

TABLE 9

Overall performance summary of 03N322R in comparison to 46A65, Q2 and 45H21 over three years.

| Comparison | Yield q/ha | % win | Yield % Checks | Days to Maturity | Plant height cm | Lodging score 1 = poor, 9 = best | Oil % | Protein % | Cholorophyll ppm | Total Gluc umol/g at 8.5% moisture | Total Saturates % | Blackleg 1 = poor, 9 = best |
|---|---|---|---|---|---|---|---|---|---|---|---|---|
| 03N322R | 29.2 | 94 | 117 | 107.0 | 117.6 | 6.0 | 51.4 | 46.5 | 27.5 | 11.7 | 6.3 | 7.6 |
| 46A65 | 24.9 |  | 100 | 106.1 | 113.4 | 6.0 | 48.3 | 46.5 | 23.3 | 15.7 | 6.4 | 7.2 |
| Loc | 62 |  | 62 | 56 | 44 | 35 | 54 | 54 | 48 | 48 | 49 | 10 |
| Diff | 4.3 |  | 18 | 0.9 | 4.2 | 0.0 | 3.2 | 0.1 | 4.1 | −4.0 | −0.1 | 0.4 |
| 03N322R | 29.2 | 89 | 118 | 107.0 | 117.6 | 6.0 | 51.4 | 46.5 | 27.5 | 11.7 | 6.3 | 7.6 |
| Q2 | 24.7 |  | 100 | 106.4 | 112.3 | 6.1 | 48.4 | 45.0 | 31.0 | 13.6 | 6.7 | 6.0 |
| Loc | 62 |  | 62 | 56 | 44 | 35 | 54 | 54 | 48 | 48 | 49 | 10 |
| Diff | 4.6 |  | 20 | 0.6 | 5.3 | −0.1 | 3.0 | 1.6 | −3.6 | −1.9 | −0.4 | 1.6 |
| 03N322R | 28.5 | 59 | 102 | 107.8 | 119.9 | 6.2 | 51.8 | 46.3 | 27.5 | 11.7 | 6.3 | 7.6 |
| 45H21 | 27.9 |  | 100 | 105.1 | 113.5 | 6.1 | 48.6 | 45.2 | 18.9 | 11.7 | 6.9 | 6.9 |
| Loc | 49 |  | 49 | 43 | 32 | 25 | 48 | 48 | 48 | 48 | 43 | 10 |
| Diff | 0.6 |  | 3 | 2.7 | 6.4 | 0.1 | 3.3 | 1.0 | 8.5 | 0.0 | −0.6 | 0.7 |

Additional yield, oil and agronomic data from co-op trials are presented in Table 10. 03N322 produced 2.7% more oil than the average of 46A65 and Q2 over two years and 26 locations. The average percent oil in the seed harvested from 03N322 was 51.1%. Information from Table 10, 11 and 12 was used for registration of the hybrid.

Disease resistance data over six locations are presented in Table 11. The blackleg disease trials were planted with a row planter where row spacing was 45-50 cm and row length was either 3 meters or 6 meters long. Each plot was comprised of a single row. Checks with known disease reaction were included as entries in the trials. Disease was encouraged by either spraying inoculum in the form of fungal spores or by spreading diseased stubble on the seedlings. Just prior to maturity, 25 plants were pulled from each row (line) in each replicate and their stems were cut open at the base and the canker development was observed. A severely damaged plant with extensive internal necrosis and poor seed set was given a score of 1. If the stem was clean, green and no sign of disease or canker or damage was seen, a score of 9 was given. The data collected on single plants were averaged for each line in each replicate and statistical analysis was carried out. The overall score for the line was obtained by averaging over all replicates and locations. Although this description applies to the trials run by the Applicant, data from other Blackleg resistance trials run by other parties is also included in the Applicant's teachings. Tables 7, 8 and 9 were trials run by the Applicant and utilized a scale of 1 to 9, with 1 being poor and 9 being best. Tables 10 and 11 show the results of trials run by Western Canadian Canola/Rapeseed Recommending Committee (WCC/RRC) and utilized a blackleg scale of 0=good and 5=poor. Finally, Table 14 shows data for the variety registration office trials, and utilizes a scale of 1=resistant and 9=highly susceptible.

46P50 was also tested for resistance to Fusarium Wilt. The Fusarium wilt trials were planted in 6 row plots, 3 meters in length, which were replicated. The trials were planted in a field with a history of Fusarium wilt disease. Just prior to physiological maturity the entries were rated for disease symptoms by examining 40 plants in the middle rows of the plots. A severely infected plant with symptoms of total necrosis on the stem and side racemes was scored as 1, while a healthy plant with a green stem was given a score of 9. The data collected on single plants was averaged for each line in each replicate and statistical analysis was carried out. The overall score for the line was obtained by averaging over all replicates.

In addition to the field data collected, there were independent data supplied by the Alberta Research Council (ARC) regarding Fusarium wilt as shown in Table 12. Their testing protocol was based on an indoor growth chamber test where they tested a plant sample of 20 over 2 replicates. For the ARC rating scale, 1=best and 9=poor.

TABLE 10

Two year agronomic performance summary for 03N322R

| Year | Variety | Yield kg/ha | Yield % of Check | Days to 50% flower | Plant Height cm | Days to Maturity | Lodging 1 = good, 5 = poor | Blackleg 0 = good 5 = poor |
|---|---|---|---|---|---|---|---|---|
| 04-Private | 03N322R | 2778 | 122 | 51.0 | 122 | 112.3 | 2.0 | 0.3 |
| 04-Private | 46A65 | 2334 | 101 | 50.0 | 119 | 110.4 | 2.1 | |
| 04-Private | Q2 | 2265 | 99 | 52.0 | 118 | 110.8 | 6.0 | |
| 04-Private | Chk Avg | 2300 | 100 | 51.0 | 119 | 110.6 | 4.0 | |
| 04-Private | Loc | 22 | 22 | 9 | 13 | 17 | 13 | 1 |
| 05-Public Co-op | 03N322R | 3713 | 115 | 48.0 | 117 | 107.2 | 2.2 | 0.6 |
| 05-Public Co-op | 46A65 | 3242 | 100 | 48.0 | 115 | 109.1 | 2.2 | |
| 05-Public Co-op | Q2 | 3222 | 100 | 49.8 | 114 | 107.0 | 2.2 | |
| 05-Public Co-op | Chk Avg | 3232 | 100 | 48.9 | 115 | 108.0 | 2.2 | |
| 05-Public Co-op | Loc | 20 | 20 | 16 | 19 | 20 | 3 | 5 |
| 2 Yr Av | 03N322R | 3223 | 118 | 49.1 | 119 | 109.5 | 2.0 | 0.5 |
| 2 Yr Av | 46A65 | 2766 | 101 | 48.7 | 117 | 109.7 | 2.1 | |
| 2 Yr Av | Q2 | 2721 | 99 | 50.6 | 116 | 108.8 | 5.3 | |
| 2 Yr Av | Chk Avg | 2744 | 100 | 49.7 | 116 | 109.2 | 3.7 | |
| | Loc | 42 | 42 | 25 | 32 | 37 | 16 | 6 |

| Year | Variety | Oil % | Protein % | Total Gluc umol/g @ 8.5% H2O | Total Saturated fat | Erucic acid % | Chlorophyll ppm | 1000 seed weight (g) |
|---|---|---|---|---|---|---|---|---|
| 04-Private | 03N322R | 52.7 | 46.3 | 14.8 | 6.3 | 0.0 | 29.2 | 3.1 |
| 04-Private | 46A65 | 49.1 | 46.6 | 17.7 | 6.4 | 0.0 | 28.5 | 3.4 |
| 04-Private | Q2 | 49.7 | 44.8 | 15.1 | 6.9 | 0.2 | 30.2 | 3.3 |
| 04-Private | Chk Avg | 49.4 | 45.7 | 16.4 | 6.7 | 0.1 | 29.4 | 3.4 |
| 04-Private | Loc | 12 | 12 | 12 | 12 | 12 | 22 | 23 |
| 05-Public Co-op | 03N322R | 49.6 | 47.5 | 9.2 | 6.5 | 0.0 | | |
| 05-Public Co-op | 46A65 | 48.1 | 46.9 | 11.8 | 6.4 | 0.1 | | |
| 05-Public Co-op | Q2 | 47.1 | 46.3 | 10.3 | 6.8 | 0.2 | | |
| 05-Public Co-op | Chk Avg | 47.6 | 46.6 | 11.1 | 6.6 | 0.1 | | |
| 05-Public Co-op | Loc | 14 | 14 | 14 | 14 | 14 | | |
| 2 Yr Av | 03N322R | 51.1 | 47.0 | 11.8 | 6.4 | 0.0 | 29.2 | |
| 2 Yr Av | 46A65 | 48.5 | 46.8 | 14.5 | 6.4 | 0.0 | 28.5 | |
| 2 Yr Av | Q2 | 48.3 | 45.6 | 12.5 | 6.8 | 0.2 | 30.2 | |
| 2 Yr Av | Chk Avg | 48.4 | 46.2 | 13.5 | 6.6 | 0.1 | 29.4 | |
| | Loc | 26 | 26 | 26 | 26 | 26 | 22 | |

Herbicide resistance data are presented in Table 13. The glyphosate herbicide screening trials were planted in four replicated split plot design where the main plots were randomized treatments (1×, 2×, Weed Free—WF) while the varieties were randomized to the sub plots. The Weed Free plot was treated with Poast™, Muster™ and Merge™. Glyphosate herbicide was sprayed at the 4-6 leaf stage. Based on five locations of herbicide resistance trials conducted over two years, it was apparent that herbicide application of glyphosate at 1× and 2× rate had no significant effect on yield, agronomic and quality traits including oil % of 46P50. As 46P50 could withstand glyphosate at the recommended rate, 46P50 is glyphosate resistant.

The morphological, agronomic and quality characteristics of the new hybrid line, 46P50, are summarized on Table 14. Table 14 compares these characteristics with those of 45H21, 46A65 and Q2. Finally, Table 15 is a summary of the commercial quality characteristics 46P50.

46P50 (03N322R) is a fully restored *Brassica napus* hybrid comprising the glyphosate resistance gene from the RT73 event, and based on the Ogura CMS system. It is a single cross hybrid produced by crossing a female parent carrying the glyphosate resistance gene by a restorer-R male line. 46P50 is the highest oil producing commercial canola hybrid developed, and also produces high grain yield per hectare resulting in the highest oil yield per hectare.

TABLE 11

Summary of blackleg rating for 03N322R and checks

| NAME | 2004 HANLEY | 2005 B. HILLS | 2005 CARMAN | 2005 N.B. | 2005 ROLAND | 2005 ROSTHERN | 2 YR AVG | % Westar | Blackleg Class |
|---|---|---|---|---|---|---|---|---|---|
| 03N322R | 0.3 | 0.3 | 0.6 | 0.4 | 1.0 | 0.6 | 0.5 | 16 | R |
| AC EXCEL | 2.8 | 2.4 | 1.3 | 1.5 | 2.7 | 1.5 | 2.0 | 58 | |
| DEFENDER | 2.3 | 1.3 | 1.4 | 1.3 | 2.5 | 1.0 | 1.6 | 47 | |
| WESTAR AVERAGE | 4.4 | 3.7 | 2.7 | 2.6 | 4.2 | 3.3 | 3.5 | 100 | |

TABLE 12

Fusarium data of 46P50 and commercial checks collected over two years

| Entry | 2004 Fusarium score 1 = poor, 9 = best | 2004 Fusarium disease incidence (0-100) | 2005 Fusarium score 1 = poor, 9 = best | 2005 Fusarium disease incidence (0-100) | Overall Fusarium score 1 = poor, 9 = best | Overall Fusarium disease incidence (0-100) | 2006 ARC Fusarium score 1 = best, 9 = poor |
|---|---|---|---|---|---|---|---|
| 45H26 | 9 | 0 | 9 | 0 | 9 | 0 | 1 |
| 46P50 | 9 | 0 | 9 | 0.7 | 9 | 0.4 | 1 |
| 45P70 | | | 9 | 0 | 9 | 0 | |
| 45H73 | | | 9 | 0 | 9 | 0 | |
| 45H21 | 9 | 0 | 9 | 0 | 9 | 0 | |
| 45A55 | 7.6 | 35 | 5.6 | 58 | 6.6 | 47 | |
| Cant 1604 | | | | | | | 6.5 |

TABLE 13

Effect of herbicide application on agronomic and quality traits of 03N322R in herbicide resistance trials in 2004 and 2005.

| Variety | Treatment | Yield q/ha | Yield (% WF) | % Stand Reduction (PCTSR) | Days to Flower | Height (cm) | Lodging at Maturity | Days to Maturity | % Oil | % Protein | Oil + Protein | Gluc's @ 8.5% | Chlorophyll |
|---|---|---|---|---|---|---|---|---|---|---|---|---|---|
| | | | | | | 2004 Morden, MB | | | | | | | |
| X03N322R | 1X | 34.6 | 96.1 | 0 | 57 | | | 112 | 54.50 | 45.00 | 99.50 | 17.00 | 9.30 |
| X03N322R | 2X | 34.4 | 95.6 | 1 | 57 | | | 112 | 55.00 | 45.00 | 100.00 | 20.00 | 13.80 |
| X03N322R | WF | 36.0 | | 0 | 57 | | | 111 | 51.00 | 50.60 | 101.60 | 19.00 | 16.00 |
| CV % | | 9.1 | | 380.0 | 0.9 | | | 1.7 | 1.90 | 2.50 | 0.60 | 5.40 | 26.90 |
| LSD (0.05) | | 4.3 | | 2.0 | 1.0 | | | 3.0 | 3.58 | 3.34 | 1.00 | 2.00 | 7.00 |
| SE | | 1.521 | | 0.707 | 0.354 | | | 1.061 | 1.266 | 1.181 | 0.354 | 0.707 | 2.475 |
| | | | | | | 2005 Morden, MB | | | | | | | |
| X03N322R | 1X | 33.8 | 98.8 | 0 | 43 | 118 | 7 | 91 | 44.49 | 51.94 | 96.43 | 13.00 | 49.00 |
| X03N322R | 2X | 33.9 | 99.1 | 0 | 43 | 120 | 7 | 90 | 43.70 | 51.95 | 95.65 | 12.00 | 33.00 |
| X03N322R | WF | 34.2 | | 0 | 43 | 119 | 7 | 88 | 44.40 | 51.24 | 95.64 | 9.00 | 23.00 |
| CV % | | 9.5 | | 774.6 | 0.8 | 5.2 | 5.4 | 2.1 | 2.20 | 1.30 | 0.70 | 12.20 | 23.40 |
| LSD (0.05) | | 4.6 | | 0.0 | 1.0 | 10.0 | 1.0 | 3.0 | 1.97 | 1.40 | 1.00 | 2.00 | 17.00 |
| SE | | 1.627 | | 0.000 | 0.354 | 3.536 | 0.354 | 1.061 | 0.697 | 0.495 | 0.354 | 0.707 | 6.011 |
| | | | | | | 2005 Saskatoon, SK | | | | | | | |
| X03N322R | 1X | 33.2 | 95.4 | 0 | 42 | 110 | | 96 | 48.71 | 49.42 | 98.13 | 9.00 | 21.00 |
| X03N322R | 2X | 33.6 | 96.6 | 0 | 42 | 108 | | 96 | 48.37 | 50.13 | 98.50 | 12.00 | 25.00 |
| X03N322R | WF | 34.8 | | 0 | 42 | 112 | | 96 | 49.76 | 49.44 | 99.20 | 9.00 | 25.00 |
| CV % | | 9.2 | | | 0.5 | 4.3 | | 0.8 | 1.40 | 1.10 | 0.70 | 9.80 | 44.90 |
| LSD (0.05) | | 6.8 | | 0.0 | 0.0 | 8.0 | | 1.0 | 2.29 | 1.59 | 1.00 | 2.00 | 18.00 |
| SE | | 2.405 | | 0.000 | 0.000 | 2.829 | | 0.354 | 0.810 | 0.562 | 0.354 | 0.707 | 6.365 |
| | | | | | | 2005 Thorsby, AB | | | | | | | |
| X03N322R | 1X | 30.3 | 112.6 | 0 | 56 | 146 | 7 | 126 | 56.21 | 42.28 | 98.49 | 13.00 | 55.00 |
| X03N322R | 2X | 29.5 | 109.7 | 0 | 57 | 139 | 7 | 127 | 56.72 | 41.33 | 98.05 | 10.00 | 73.00 |
| X03N322R | WF | 26.9 | | 0 | 56 | 136 | 7 | 125 | 55.66 | 40.73 | 96.39 | 10.00 | 77.00 |
| CV % | | 6.1 | | 126.5 | 1.3 | 6.6 | 9.6 | 1.9 | 1.30 | 1.80 | 0.50 | 9.40 | 21.10 |
| LSD (0.05) | | 6.0 | | 1.0 | 1.0 | 16.0 | 1.0 | 4.0 | 2.74 | 1.76 | 2.00 | 2.00 | 29.00 |
| SE | | 2.122 | | 0.354 | 0.354 | 5.658 | 0.354 | 1.414 | 0.969 | 0.622 | 0.707 | 0.707 | 10.255 |
| | | | | | | 2005 Ellerslie, AB | | | | | | | |
| X03N322R | 1X | 38.1 | 100.0 | 1 | 53 | 115 | 8 | 118 | 56.51 | 40.39 | 96.90 | 6.00 | 53.00 |
| X03N322R | 2X | 37.8 | 99.2 | 1 | 53 | 117 | 8 | 120 | 58.08 | 40.12 | 98.20 | 7.00 | 33.00 |
| X03N322R | WF | 38.1 | | 0 | 52 | 121 | 8 | 117 | 57.03 | 41.60 | 98.63 | 8.00 | 25.00 |
| CV % | | 8.6 | | 72.3 | 1.0 | 4.4 | 8.2 | 1.6 | 1.10 | 1.70 | 0.60 | 9.70 | 39.60 |
| LSD (0.05) | | 4.5 | | 0.0 | 1.0 | 9.0 | 1.0 | 3.0 | 1.35 | 1.80 | 1.00 | 2.00 | 22.00 |
| SE | | 1.591 | | 0.000 | 0.354 | 3.182 | 0.354 | 1.061 | 0.477 | 0.636 | 0.354 | 0.707 | 7.779 |
| | | | | | | 2005 Average | | | | | | | |
| X03N322R | 1X | 33.7 | 100.6 | 0 | 48 | 121 | 7 | 108 | 51.48 | 46.01 | 97.49 | 10.00 | 45.00 |
| X03N322R | 2X | 33.7 | 100.6 | 0 | 49 | 121 | 7 | 108 | 51.72 | 45.89 | 97.61 | 10.00 | 41.00 |
| X03N322R | WF | 33.5 | | 0 | 48 | 122 | 7 | 107 | 51.71 | 45.75 | 97.46 | 9.00 | 38.00 |
| CV % | | 9.2 | | 140.6 | 1.4 | 5.8 | 8.6 | 1.8 | 2.10 | 1.80 | 0.90 | 14.20 | 34.40 |
| LSD (0.05) | | 2.7 | | 0.0 | 0.0 | 6.0 | 1.0 | 1.0 | 1.21 | 0.93 | 1.00 | 1.00 | 13.00 |
| SE | | 0.955 | | 0.000 | 0.000 | 2.122 | 0.354 | 0.354 | 0.428 | 0.329 | 0.354 | 0.354 | 4.597 |
| Locations | | 4 | | 4 | 4 | 4 | 3 | 4 | 4 | 4 | 4 | 4 | 4 |
| | | | | | | 2 year average | | | | | | | |
| X03N322R | 1X | 34.0 | 100.0 | 0.2 | 50.2 | 122.3 | 7.3 | 108.6 | 52.20 | 45.60 | 97.80 | 10.25 | 37.40 |
| X03N322R | 2X | 34.0 | 100.0 | 0.4 | 50.4 | 121.0 | 7.3 | 109.0 | 52.40 | 45.60 | 98.00 | 10.25 | 35.60 |

TABLE 13-continued

Effect of herbicide application on agronomic and quality traits of 03N322R in herbicide resistance trials in 2004 and 2005.

| Variety | Treatment | Yield q/ha | Yield (% WF) | % Stand Reduction (PCTSR) | Days to Flower | Height (cm) | Lodging at Maturity | Days to Maturity | % Oil | % Protein | Oil + Protein | Gluc's @ 8.5% | Chlorophyll |
|---|---|---|---|---|---|---|---|---|---|---|---|---|---|
| X03N322R | WF | 34.0 | | 0.0 | 50.0 | 122.0 | 7.3 | 107.4 | 51.60 | 46.80 | 98.40 | 9.00 | 33.20 |
| CV % | | 9.2 | | 123.7 | 1.4 | 0.0 | 0.0 | 2.2 | 4.62 | 4.73 | 2.29 | 0.00 | 26.23 |
| LSD (0.05) | | 1.1 | | 0.1 | 0.5 | 2.7 | 0.4 | 1.1 | 0.96 | 1.12 | 0.86 | 2.11 | 15.64 |
| SE | | 0.396 | | 0.033 | 0.163 | 0.965 | 0.157 | 0.382 | 0.340 | 0.396 | 0.303 | 0.746 | 5.530 |
| Locations | | 5 | | 5 | 5 | 4 | 3 | 5 | 5 | 5 | 5 | 5 | 5 |

TABLE 14

Description of morphological, agronomic and quality traits for 46P50
Variety Name: 46P50 Tested as: 03N322R

| Trait Code | Trait | 03N322R mean | 03N322R description* | 45H21 mean | 45H21 description* | 46A65 mean | 46A65 description* | Q2 mean | Q2 description* |
|---|---|---|---|---|---|---|---|---|---|
| 2.0 | Seasonal Type | 1 | Spring | 1 | Spring | 1 | Spring | 1 | Spring |
| 3.1 | cot width (mm) | 22.12 | wide | 20.72 | wide | 18.30 | medium | 19.62 | medium |
| | cot length (mm) | 11.38 | long | 10.06 | long | 9.20 | medium | 9.10 | medium |
| 3.6 | blade colour (1 = lgt.gm- 4 = blue.gm) | 2.8 | medium to dark green | 3.0 | dark green | 2.5 | medium to dark green | 3.3 | dark green |
| | leaf: percentage of lobed leaves (%) | 87% | | 93% | | 83% | | 60% | |
| 3.4 | lobe development (1 = absent(entire)-2 = present (lobed)) | 2.00 | present | 2.00 | present | 2.00 | present | 2 | present |
| | number of lobes (1 = v.few- 9 = v.many) | 3.00 | few | 3.00 | few | 3.00 | few | 2.00 | very few |
| | number of lobes (count) | 2.77 | few | 3.43 | few | 3.30 | few | 2.03 | very few |
| | margin type (1 = undulating- 3 = sharp) | 3.0 | sharp | 2.8 | rounded to sharp | 2.7 | rounded to sharp | 2.8 | rounded to sharp |
| 3.5 | indentation of margin | 5.0 | medium | 3.7 | shallow | 5.0 | medium | 3.7 | shallow |
| | leaf length (cm) | 22.13 | medium | 24.04 | medium | 20.86 | medium | 23.23 | medium |
| | leaf width (cm) | 11.38 | medium | 12.42 | medium to wide | 10.93 | medium | 12.16 | medium to wide |
| | leaf length:width rati | 1.95 | | 1.94 | | 1.93 | | 1.92 | |
| | petiole length (cm) | 5.83 | short | 8.85 | medium | 6.69 | short to medium | 4.45 | short |
| 3.3 | stem anthocyanin | 1.0 | absent | 1.0 | absent | 1.0 | absent | 1.0 | absent |
| 3.8 | leaf glaucosity | 2.2 | weak | 2.3 | weak | 2.2 | weak | 2.5 | weak |
| 4.1 | flower date 50% | 50.0 | medium | 51.0 | medium | 51.0 | medium | 52.0 | medium |
| 4.5 | petal colour (1 = white- 4 = orange, 5 = other) | 3.00 | medium yellow | 3.00 | medium yellow | 3.00 | medium yellow | 3.00 | medium yellow |
| | petal length (mm) | 13.20 | medium | 13.20 | medium | 13.83 | medium | 13.33 | medium |
| | petal width (mm) | 6.20 | medium | 6.10 | medium | 6.40 | medium | 6.30 | medium |
| | petal length:width ratio | 2.15 | | 2.18 | | 2.18 | | 2.14 | |
| 4.8 | anther fertility (1 = sterile, 2 = shedding pollen) | 2.00 | shedding pollen | 2.00 | shedding pollen | 2.00 | shedding pollen | 2.00 | shedding pollen |
| 4.12 | silque attitude (1 = erect- 9 = drooping) | 2.5 | erect to semi-erect | 2.3 | erect to semi-erect | 2.7 | erect to semi-erect | 4.0 | semi-erect to horizontal |
| 4.1 | silque length (1 = v.short- 9 = v.long) | 5.00 | medium | 6.00 | medium | 5.00 | medium | 8.00 | long |
| 4.1 | silque length (mm) | 57.75 | medium | 64.30 | medium | 54.22 | medium | 71.92 | long |
| 4.11 | silque width (1 = v.narrow- 9 = v.wide) | 5.00 | medium | 4.50 | narrow to medium | 5.00 | medium | 5.00 | medium |
| 4.11 | silque width (mm) | 5.43 | medium | 4.97 | narrow to medium | 5.03 | medium | 5.22 | medium |
| 4.13 | beak length (1 = v.short- 9 = v.long) | 3.00 | short | 3.00 | short | 5.00 | medium | 3.00 | short |
| 4.13 | beak length (mm) | 7.23 | short | 7.12 | short | 8.18 | medium | 7.10 | short |
| 4.14 | pedicel length (1 = v.short- 9 = v.long) | 5.00 | medium | 6.00 | medium to long | 6.00 | medium to long | 4.00 | short to medium |
| 4.14 | pedicel length (mm) | 18.48 | medium | 21.10 | medium to long | 20.73 | medium to long | 17.60 | short to medium |
| 4.15 | maturity (days from planting) | 106.7 | medium | 104.0 | medium | 106.7 | medium | 106.4 | medium |
| 4.2 | plant height (1 = v.short-9 = v.tall) | 7.00 | tall | 6.00 | medium | 6.00 | medium | 5.00 | medium |
| 4.2 | plant height (cm) | 118.10 | tall | 112.50 | medium | 113.70 | medium | 110.60 | medium |
| 5.1 | seed coat colour (1 = blk, 2 = brn, 3 = yel, 4 = mix, 5 = oth) | 1.50 | black to brown | 1.50 | black to brown | 1.50 | black to brown | 1.50 | black to brown |
| 5.3 | seed weight (grams per 1000 seeds) | 3.51 | medium | 3.90 | medium to large | 3.65 | medium | 3.62 | medium |

TABLE 14-continued

Description of morphological, agronomic and quality traits for 46P50
Variety Name: 46P50 Tested as: 03N322R

| Trait Code | Trait | 03N322R mean | description* | 45H21 mean | description* | 46A65 mean | description* | Q2 mean | description* |
|---|---|---|---|---|---|---|---|---|---|
| 6.1 | resistance to shattering (3 = poor, 7 = good) | 9.00 | v. good | 9.00 | v. good | 9.00 | v. good | 9.00 | v. good |
| 6.2 | resistance to lodging (3 = poor, 7 = good) | 6.50 | medium to good | 6.60 | medium to good | 6.80 | medium to good | 6.60 | medium to good |
| 10.2 | percentage of total fatty acids-eurcic (C22:1) | 0.02 | very low | 0.01 | very low | 0.02 | very low | 0.20 | very low |
| 10.3 | Maximum allowable erucic in foundation seed = 0.5% | | | | | | | | |
| 10.7 | glucosinolates (u mole-total aliphtic glucs/g airdryed meal)-very low (<10), low (10-15), med (15-20), high (>20) | 9.24 | very low | 10.19 | low | 13.67 | low | 11.60 | low |
| 10.9 | chlorophyll content (ppm) low (<8), med (8-15), high (>15) (ppm) | 27.86 | high | 13.94 | medium | 19.38 | high | 32.18 | high |
| 10.1 | oil percentage (whole dry seed) | 52.11 | | 48.79 | | 48.92 | | 49.23 | |
| 10.5 | protein percentage (whole dry seed) | 46.20 | | 44.91 | | 45.97 | | 44.51 | |
| 7.4 | blackleg resistance (0 = not tested, 1 = resistant, 9 = highly susceptible) | 0.2 | resistant | 0.4 | resistant | 0.3 | resistant | 1.7 | moderately resistant |
| 7.10 | white rust (2 V and 7 V) (0 = not tested, 1 = resistant, 9 = highly susceptible) | 1.00 | resistant | 1.00 | resistant | 1.00 | resistant | 1.00 | resistant |
| 8.3 | Glyphosate (0-not tested, 1-resistant, 5-tolerant, 9-susceptible) | 1.00 | resistant | 1.00 | resistant | 9.00 | susceptible | 9.00 | susceptible |

*VARIETY DESCRIPTIONS BASED ON MORPHOLOGICAL, AGRONOMIC AND QUALITY TRAITS PREPARED FOR THE VARIETY REGISTRATION OFFICE (VRO) MORPHOLOGICAL DATA FROM 2005 ONT., AGRONOMIC AND QUALITY DATA FROM 2005 W. CANADA

TABLE 15

Summary of the commercial quality characteristics of 46P50

| | |
|---|---|
| Seed Yield: | Eighteen percent higher than WCC/RRC checks. |
| Disease Reaction: | Classified as Resistant (R = same class as 46A65) to blackleg (*Leptospaera maculans*) according to WCC/RRC guidelines.. Based on Pioneer Hi-Bred trials, 46P50 (03N322R) is also resistant (R) to Fusarium wilt. |
| Plant Height: | slightly taller than WCC/RRC checks. |
| Maturity: | similar maturity as WCC/RRC checks. |
| Lodging: | Better standability than of checks. |
| Herbicide resistance: | resistant to glyphosate herbicides; field test confirms that 46P50 (03N322R) tolerates the recommended rate of glyphosate(1.5 L/ha) without showing plant injury or any significant negative effect on yield, agronomic and quality traits.. |
| Seed color: | dark brown. |
| Grain size: | 1000 seed weight is slightly less than WCC/RRC checks. |
| Seed oil content: | 2.8% higher than mean of the checks. |
| Seed protein content: | 0.8% higher than mean of the checks. |
| Erucic acid: | less than 0.5% (maximum allowable limit). |
| Total saturates: | Lower than WCC/RRC checks (meets WCC/RRC requirements). |
| Total glucosinolates: | less than mean of the checks (meets WCC/RRC requirements). |
| Chlorophyll: | similar to mean of the checks. |
| Summary: | 46P50 (03N322R) is a medium maturing, glyphosate resistant *Brassica napus* canola hybrid having resistant "R" rating for blackleg and resistant "R" rating for Fusarium wilt. It has extremely high oil contents which is 2.8% higher than mean of the checks. Its protein is 0.8% higher than mean of the checks and chlorophyll is similar to checks. |

46P50 produces, on average, between about 2.7% to 3.3% higher oil content compared to the registration checks. Accordingly, 46P50 can produce, on average, between about 2.8% and 3.2%, or between about 2.9% and 3.1%, or about 3% greater oil content compared to registration checks, when the checks are grown under the same environmental conditions, and the percent oil is calculated at 0% moisture. There is no commercial canola variety or hybrid registered in Canada that yields this level of oil. The two inbred lines involved in the production of this hybrid also have higher oil than other inbred parents. The increase in oil has come from the steady improvement in oil content in both female and male parents by the technical intervention by man. The invention encompasses hybrid seed designated 46P50, and the hybrid plant thereof, as well as the F2 seed produced on the hybrid plant. Also encompassed in the invention is the oil and/or meal of the F2 seed produced on the 46P50 hybrid plant. Further, any plant part, including cells, from 46P50 seed or hybrid plant thereof, or a plant part from a progeny, descendent, sub-line or offspring derived from 46P50 or from a line obtained by crossing 46P50 to a second *Brassica* plant, is also encompassed in the invention.

The invention encompasses any plant part of 46P50, or a descendent or a sub-line thereof, or a plant produced by crossing 46P50 with a second plant. The plant part can be any plant part, for example, but not limited to pollen, an ovule, a grain, a cell, a protoplast, and a regenerable cell or protoplast. Further encompassed in the invention are tissue cultures of 46P50, or a descendent or sub-line thereof, or from a plant produced by crossing 46P50 with a second plant. Tissue culture methods for *Brassica* are well known to those of skill in the art (see, for example, Huang, B. (1992) Genetic manipulation of microspores and microspore-derived embryos. *In Vitro Cell Dev. Biol.* 28:53-58; Moloney, et al., "High Efficiency Transformation of *Brassica napus* using *Agrobacterium* vectors" *Plant Cell Reports* (1989) 8:238-242; and Radke, et al., Transformation and Regeneration of *Brassica rapa* using Agrobacterium Vectors" *Plant Cell Reports* (1992) 11:499-505, all of which are herein incorporated by reference.

The invention also encompasses any genetically modified plant that is a descendent or a sub-line of 46P50. The genetically modified plant would express a foreign gene or transcription cassette not normally associated with *Brassica* genomes. Transformation methods for *Brassicas* are known to those skilled in the art (for example, U.S. Pat. No. 6,297,056 incorporated herein by reference).

The advent of new molecular biological techniques have allowed the isolation and characterization of genetic elements with specific functions, such as encoding specific protein products. Scientists in the field of plant biology developed a strong interest in engineering the genome of plants to contain and express foreign genetic elements, or additional, or modified versions of native or endogenous genetic elements in order to alter the traits of a plant in a specific manner. Any DNA sequences, whether from a different species or from the same species, that are inserted into the genome using transformation are referred to herein collectively as "transgenes". Over the last fifteen to twenty years several methods for producing transgenic plants have been developed, and the present invention, in particular embodiments, also relates to transformed versions of the claimed canola hybrid 46P50.

Numerous methods for plant transformation have been developed, including biological and physical, plant transformation protocols. See, for example, Miki, et al., "Procedures for Introducing Foreign DNA into Plants" in Methods in Plant Molecular Biology and Biotechnology, Glick, B. R. and Genetic Transformation for the improvement of Canola World Conf, Biotechnol Fats and Oils Ind. 4346, 1988. In addition, expression vectors and in vitro culture methods for plant cell or tissue transformation and regeneration of plants are available. See, for example, Gruber, et al., "Vectors for Plant Transformation" in Methods in Plant Molecular Biology and Biotechnology, Glick, B. R. and Thompson, J. E. Eds. (CRC Press, Inc., Boca Raton, 1993) pages 89-119.

The most prevalent types of plant transformation involve the construction of an expression vector. Such a vector comprises a DNA sequence that contains a gene under the control of or operatively linked to a regulatory element, for example a promoter. The vector may contain one or more genes and one or more regulatory elements.

A genetic trait which has been engineered into a particular canola plant using transformation techniques, could be moved into another line using traditional breeding techniques that are well known in the plant breeding arts. For example, a backcrossing approach could be used to move a transgene from a transformed canola plant to an elite inbred line or hybrid and the resulting progeny would comprise a transgene. Alternatively, the hybrid can be transformed directly. As used herein, "crossing" can refer to a simple X by Y cross, or the process of backcrossing, depending on the context. Various genetic elements can be introduced into the plant genome using transformation. These elements include but are not limited to genes; coding sequences; inducible, constitutive, and tissue specific promoters; enhancing sequences; and signal and targeting sequences. See, U.S. Pat. No. 6,222,101 which is herein incorporated by reference.

With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign protein then can be extracted from a tissue of interest or from total biomass. Protein extraction from plant biomass can be accomplished by known methods which are discussed, for example, by Heney and Orr, (1981) *Anal. Biochem* 114:92-6.

A genetic map can be generated, primarily via conventional Restriction Fragment Length Polymorphisms (RFLP), Polymerase Chain Reaction (PCR) analysis, and Simple Sequence Repeats (SSR) which identifies the approximate chromosomal location of the integrated DNA molecule coding for the foreign protein. For exemplary methodologies in this regard, see, Glick and Thompson, *Methods In Plant Molecular Biology And Biotechnology* 269-284 (CRC Press, Boca Raton, 1993). Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons would involve hybridizations, RFLP, PCR, SSR and sequencing, all of which are conventional techniques.

Likewise, by means of the present invention, plants can be genetically engineered to express various phenotypes of agronomic interest. Exemplary transgenes implicated in this regard include, but are not limited to, those categorized below.

1. Genes that Confer Resistance to Pests or Disease and that Encode (A) Plant disease resistance genes. Plant defenses are often activated by specific interaction between the product of a disease resistance gene (R) in the plant and the product of a corresponding avirulence (Avr) gene in the pathogen. A plant variety can be transformed with a cloned resistance gene to engineer plants that are resistant to specific pathogen strains. See, for example, Jones, et al., (1994) *Science* 266:789 (cloning of the tomato Cf-9 gene for resistance to *Cladosporium fulvum*); Martin, et al., (1993) *Science* 262:1432 (tomato Pto gene for resistance to *Pseudomonas syndngae* pv. tomato encodes a protein kinase); Mindrinos, et al., (1994) *Cell* 78:1089 (*Arabidopsis* RSP2 gene for resistance to *Pseudomonas syringae*), McDowell and Woffenden, (2003) *Trends Biotechnol.* 21(4):178-83 and Toyoda, et al., (2002) *Transgenic Res.* 11(6):567-82. A plant resistant to a disease is one that is more resistant to a pathogen as compared to the wild type plant.

(B) A gene conferring resistance to fungal pathogens, such as oxalate oxidase or oxalate decarboxylase (Zhou, et al., (1998) Pi. Physiol. 117(1):3341).

(C) A *Bacillus thuringiensis* protein, a derivative thereof or a synthetic polypeptide modeled thereon. See, for example, Geiser, et al., (1986) *Gene* 48:109, who disclose the cloning and nucleotide sequence of a Bt delta-endotoxin gene. Moreover, DNA molecules encoding delta-endotoxin genes can be purchased from American Type Culture Collection (Manassas, Va.), for example, under ATCC Accession Numbers 40098, 67136, 31995 and 31998. Other examples of *Bacillus thuringiensis* transgenes being genetically engineered are given in the following patents and patent applications and hereby are incorporated by reference for this purpose: U.S. Pat. Nos. 5,188,960; 5,689,052; 5,880,275; WO 91/114778; WO 99/31248; WO 01/12731; WO 99/24581; WO 97/40162 and U.S. application Ser. Nos. 10/032,717; 10/414,637; and 10/606,320.

(D) An insect-specific hormone or pheromone such as an ecdysteroid and juvenile hormone, a variant thereof, a mimetic based thereon, or an antagonist or agonist thereof. See, for example, the disclosure by Hammock, et al., (1990) *Nature* 344:458, of baculovirus expression of cloned juvenile hormone esterase, an inactivator of juvenile hormone.

(E) An insect-specific peptide which, upon expression, disrupts the physiology of the affected pest. For example, see the disclosures of Regan, (1994) *J. Biol. Chem.* 269:9 (expression cloning yields DNA coding for insect diuretic hormone receptor), and Pratt, et al., (1989) *Biochem. Biophys. Res. Comm.* 163:1243 (an allostatin is identified in *Diploptera puntata*); Chattopadhyay, et al., (2004) *Critical Reviews in Microbiology* 30(1):33-54; Zjawiony (2004) *J Nat Prod* 67(2):300-310; Carlini and Grossi-de-Sa (2002) *Toxicon* 40(11):1515-1539; Ussuf, et al., (2001) *Curr Sci.* 80(7): 847-853; and Vasconcelos and Oliveira (2004) *Toxicon* 44(4): 385-403). See also, U.S. Pat. No. 5,266,317 to Tomalski, et al., who disclose genes encoding insect-specific, paralytic neurotoxins.

(F) An enzyme responsible for a hyperaccumulation of a monterpene, a sesquiterpene, a steroid, hydroxamic acid, a phenylpropanoid derivative or another non-protein molecule with insecticidal activity.

(G) An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO 93/02197 in the name of Scott, et al., which discloses the nucleotide sequence of a callase gene. DNA molecules which contain chitinase-encoding sequences can be obtained, for example, from the ATCC under Accession Nos. 39637 and 67152. See also, Kramer, et al., (1993) *Insect Biochem. Molec. Biol.* 23:691, who teach the nucleotide sequence of a cDNA encoding tobacco hookworm chitinase, and Kawalleck, et al., (1993) *Plant Molec. Biol.* 21:673, who provide the nucleotide sequence of the parsley ubi4-2 polyubiquitin gene, U.S. application Ser. Nos. 10/389,432, 10/692,367, and U.S. Pat. No. 6,563,020.

(H) A molecule that stimulates signal transduction. For example, see the disclosure by Botella, et al., (1994) *Plant Molec. Biol.* 24:757, of nucleotide sequences for mung bean calmodulin cDNA clones, and Griess, et al., (1994) *Plant Physiol.* 104:1467, who provide the nucleotide sequence of a maize calmodulin cDNA clone.

(I) A hydrophobic moment peptide. See, PCT application WO95/16776 and U.S. Pat. No. 5,580,852 (disclosure of peptide derivatives of Tachyplesin which inhibit fungal plant pathogens) and PCT application WO95/18855 and U.S. Pat. No. 5,607,914 (teaches synthetic antimicrobial peptides that confer disease resistance), the respective contents of which are hereby incorporated by reference for this purpose.

(J) A membrane permease, a channel former or a channel blocker. For example, see the disclosure by Jaynes, et al., (1993) *Plant Sci.* 89:43, of heterologous expression of a cecropin-beta lytic peptide analog to render transgenic tobacco plants resistant to *Pseudomonas solanacearum*.

(K) A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy, et al., (1990) *Ann. Rev. Phytopathol.* 28:451. Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

(L) An insect-specific antibody or an immunotoxin derived therefrom. Thus, an antibody targeted to a critical metabolic function in the insect gut would inactivate an affected enzyme, killing the insect. Cf. Taylor, et al., Abstract #497, SEVENTH INT'L SYMPOSIUM ON MOLECULAR PLANT-MICROBE INTERACTIONS (Edinburgh, Scotland, 1994) (enzymatic inactivation in transgenic tobacco via production of single-chain antibody fragments).

(M) A virus-specific antibody. See, for example, Taviadoraki, et al., (1993) *Nature* 366:469, who show that transgenic plants expressing recombinant antibody genes are protected from virus attack.

(N) A developmental-arrestive protein produced in nature by a pathogen or a parasite. Thus, fungal endo alpha-1,4-D-polygalacturonases facilitate fungal colonization and plant nutrient release by solubilizing plant cell wall homo-alpha-1,4-D-galacturonase. See, Lamb, et al., (1992) *Bio/Technology* 10:1436. The cloning and characterization of a gene which encodes a bean endopolygalacturonase-inhibiting protein is described by Toubart, et al., (1992) *Plant J.* 2:367.

(O) A developmental-arrestive protein produced in nature by a plant. For example, Logemann, et al., (1992) *Bio/Technology* 10:305, have shown that transgenic plants expressing the barley ribosome-inactivating gene have an increased resistance to fungal disease.

(P) Genes involved in the Systemic Acquired Resistance (SAR) Response and/or the pathogenesis related genes. Briggs, S., (1995) *Current Biology* 5(2), Pieterse and Van Loon (2004) *Curr. Opin. Plant Bio.* 7(4):456-64 and Somssich (2003) *Cell* 113(7):815-6.

(Q) Antifungal genes. Cornelissen and Melchers, (1993) *Pl. Physiol.* 101:709-712, and Parijs, et al., (1991) *Planta* 183:258-264, and Bushnell, et al., (1998) *Can. J. of Plant Path.* 20(2):137-149. Also see, U.S. application Ser. No. 09/950,933.

(R) Detoxification genes, such as for fumonisin, beauvericin, moniliformin and zearalenone and their structurally related derivatives. For example, see U.S. Pat. No. 5,792,931.

(S) Cystatin and cysteine proteinase inhibitors. See, U.S. application Ser. No. 10/947,979.

(T) Defensin genes. See, WO03000863 and U.S. application Ser. No. 10/178,213.

(U) Genes that confer resistance to *Phytophthora* Root Rot, such as the *Brassica* equivalents of the Rps 1, Rps 1-a, Rps 1-b, Rps 1-c, Rps 1-d, Rps 1-e, Rps 1-k, Rps 2, Rps 3-a, Rps 3-b, Rps 3-c, Rps 4, Rps 5, Rps 6, Rps 7 and other Rps genes. See, for example, Shoemaker, et al., *Phytophthora* Root Rot Resistance Gene Mapping in Soybean, Plant Genome IV Conference, San Diego, Calif. (1995).

2. Genes that Confer Resistance to a Herbicide, for Example (A) A herbicide that inhibits the growing point or meristem, such as an imidazalinone or a sulfonylurea. Exemplary genes in this category code for mutant ALS and AHAS enzyme as described, for example, by Lee, et al., (1988) *EMBO J.* 7:1241, and Miki, et al., (1990) *Theor. Appl. Genet* 80:449, respectively. See also, U.S. Pat. Nos. 5,605,011; 5,013,659; 5,141,870; 5,767,361; 5,731,180; 5,304,732; 4,761,373; 5,331,107; 5,928,937; and 5,378,824; and international publication WO 96/33270, which are incorporated herein by reference for this purpose.

(B) Glyphosate (resistance imparted by mutant 5-enolpyruvl-3-phosphikimate synthase (EPSP) and aroA genes, respectively) and other phosphono compounds such as glufosinate (phosphinothricin acetyl transferase, PAT) and *Streptomyces hygroscopicus* phosphinothricin-acetyl transferase, bar, genes), and pyridinoxy or phenoxy propionic acids and cycloshexones (ACCase inhibitor-encoding genes). See, for example, U.S. Pat. No. 4,940,835 to Shah, et al., which discloses the nucleotide sequence of a form of EPSP which can confer glyphosate resistance. U.S. Pat. No. 5,627, 061 to Barry, et al., also describes genes encoding EPSPS enzymes. See also, U.S. Pat. Nos. 6,566,587; 6,338,961; 6,248,876 B1; 6,040,497; 5,804,425; 5,633,435; 5,145,783; 4,971,908; 5,312,910; 5,188,642; 4,940,835; 5,866,775; 6,225,114 B1; 6,130,366; 5,310,667; 4,535,060; 4,769,061; 5,633,448; 5,510,471; Re. 36,449; RE 37,287 E; and 5,491, 288; and international publications EP1173580; WO 01/66704; EP1173581 and EP1173582, which are incorporated herein by reference for this purpose. Glyphosate resistance may also be conferred by glyphosate N-acetyl transferase (GAT) genes: see for example, WO2002/36782 or WO2005/012515; US patent publications 20040082770, 20050246798, 20060200874, 20060191033, 20060218663 and 20070004912; and Canadian patent applications 2,521, 284 and 2,425, 956 all of which are herein incorporated by reference. A DNA molecule encoding a mutant aroA gene can be obtained under ATCC accession No. 39256, and the nucleotide sequence of the mutant gene is disclosed in U.S. Pat. No. 4,769,061 to Comai. European patent application Number 0 333 033 to Kumada, et al., and U.S. Pat. No. 4,975,374 to Goodman, et al., disclose nucleotide sequences of glutamine synthetase genes which confer resistance to herbicides such as L-phosphinothricin. The nucleotide sequence of a phosphinothricin-acetyl-transferase gene is provided in European application number 0 242 246 to Leemans, et al.; De Greef, et al., (1989) *Bio/Technology* 7:61, describe the production of transgenic plants that express chimeric bar genes coding for phosphinothricin acetyl transferase activity. See also, U.S. Pat. Nos. 5,969,213; 5,489,520; 5,550,318; 5,874,265; 5,919, 675; 5,561,236; 5,648,477; 5,646,024; 6,177,616 B1; and 5,879,903, which are incorporated herein by reference for this purpose. Exemplary of genes conferring resistance to phenoxy propionic acids and cycloshexones, such as sethoxydim and haloxyfop, are the Acc1-S1, Acc1-S2 and Acc1-S3 genes described by Marshall, et al., (1992) *Theor. Appl. Genet* 83:435. See also, U.S. Pat. Nos. 5,188,642; 5,352,605; 5,530, 196; 5,633,435; 5,717,084; 5,728,925; 5,804,425; and Canadian Patent Number 1,313,830, which are incorporated herein by reference for this purpose.

(C) A herbicide that inhibits photosynthesis, such as a triazine (psbA and gs+ genes) and a benzonitrile (nitrilase gene). Przibilla, et al., (1991) *Plant Cell* 3:169, describe the transformation of Chlamydomonas with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441 and 67442. Cloning and expression of DNA coding for a glutathione S-transferase is described by Hayes, et al., (1992) *Biochem. J.* 285:173.

(D) Acetohydroxy acid synthase, which has been found to make plants that express this enzyme resistant to multiple types of herbicides, has been introduced into a variety of plants (see, e.g., Hattori, et al., (1995) *Mol Gen Genet* 246: 419). Other genes that confer tolerance to herbicides include: a gene encoding a chimeric protein of rat cytochrome P4507A1 and yeast NADPH-cytochrome P450 oxidoreductase (Shiota, et al., (1994) *Plant Physiol* 106:17), genes for glutathione reductase and superoxide dismutase (Aono, et al., (1995) *Plant Cell Physiol* 36:1687, and genes for various phosphotransferases (Datta, et al., (1992) *Plant Mol Biol* 20:619).

(E) Protoporphyrinogen oxidase (protox) is necessary for the production of chlorophyll, which is necessary for all plant survival. The protox enzyme serves as the target for a variety of herbicidal compounds. These herbicides also inhibit growth of all the different species of plants present, causing their total destruction. The development of plants containing altered protox activity which are resistant to these herbicides are described in U.S. Pat. Nos. 6,288,306 B1; 6,282,837 B1; and 5,767,373; and international publication WO 01/12825, which are incorporated herein by reference for this purpose.

3. Transgenes that Confer or Contribute to an Altered Grain Characteristic, Such as (A) Altered fatty acids, for example, by
(1) Down-regulation of stearoyl-ACP desaturase to increase stearic acid content of the plant. See, Knultzon, et al., (1992) *Proc. Natl. Acad. Sci. USA* 89:2624 and WO99/64579 (Genes for Desaturases to Alter Lipid Profiles in Corn),
(2) Elevating oleic acid via FAD-2 gene modification and/or decreasing linolenic acid via FAD-3 gene modification (see, U.S. Pat. Nos. 6,063,947; 6,323,392; 6,372,965 and WO 93/11245),
(3) Altering conjugated linolenic or linoleic acid content, such as in WO 01/12800,
(4) Altering LEC1, AGP, Dek1, Superal1, mi1ups, various Ipa genes such as Ipa1, Ipa3, hpt or hggt. For example, see. WO 02/42424, WO 98/22604, WO 03/011015, U.S. Pat. No. 6,423,886, U.S. Pat. No. 6,197,561, U.S. Pat. No. 6,825,397, US2003/0079247, US2003/0204870, WO02/057439, WO03/011015 and Rivera-Madrid, et al., (1995) *Proc. Natl. Acad. Sci.* 92:5620-5624.

(B) Altered phosphorus content, for example, by the
(1) Introduction of a phytase-encoding gene would enhance breakdown of phytate, adding more free phosphate to the transformed plant. For example, see, Van Hartingsveldt, et al., (1993) *Gene* 127:87, for a disclosure of the nucleotide sequence of an *Aspergillus niger* phytase gene.
(2) Up-regulation of a gene that reduces phytate content. In maize, this, for example, could be accomplished, by cloning and then re-introducing DNA associated with one or more of the alleles, such as the LPA alleles, identified in maize mutants characterized by low levels of phytic acid, such as in Raboy, et al., (1990) *Maydica* 35:383 and/or by altering inositol kinase activity as in WO 02/059324, US2003/0009011, WO 03/027243, US2003/0079247, WO 99/05298, U.S. Pat. No. 6,197,561, U.S. Pat. No. 6,291,224, U.S. Pat. No. 6,391, 348, WO2002/059324, US2003/0079247, Wo98/45448, WO99/55882, WO01/04147.

(C) Altered carbohydrates effected, for example, by altering a gene for an enzyme that affects the branching pattern of starch, a gene altering thioredoxin. (See, U.S. Pat. No. 6,531, 648). See, Shiroza, et al., (1988) *J. Bacteriol.* 170:810 (nucleotide sequence of *Streptococcus mutans* fructosyltransferase gene), Steinmetz, et al., (1985) *Mol. Gen. Genet.* 200:220 (nucleotide sequence of *Bacillus subtilis* levansucrase gene), Pen, et al., (1992) *Bio/Technology* 10:292 (production of transgenic plants that express *Bacillus licheniformis* alpha-amylase), Elliot, et al., (1993) *Plant Molec. Biol.* 21:515 (nucleotide sequences of tomato invertase genes), Sogaard, et al., (1993) *J. Biol. Chem* 268:22480 (site-directed mutagenesis of barley alpha-amylase gene), and Fisher, et al., (1993) *Plant Physiol.* 102:1045 (maize endosperm starch branching enzyme II), WO 99/10498 (improved digestibility and/or starch extraction through modification of UDP-D-xylose 4-epimerase, Fragile 1 and 2, Ref1, HCHL, C4H), U.S. Pat. No. 6,232,529 (method of producing high oil seed by modification of starch levels (AGP)). The fatty acid modification genes mentioned above may also be used to affect starch content and/or composition through the interrelationship of the starch and oil pathways.

(D) Altered antioxidant content or composition, such as alteration of tocopherol or tocotrienols. For example, see, U.S. Pat. No. 6,787,683, US2004/0034886 and WO 00/68393 involving the manipulation of antioxidant levels through alteration of a phytl prenyl transferase (ppt), WO 03/082899 through alteration of a homogentisate geranyl geranyl transferase (hggt).

(E) Altered essential seed amino acids. For example, see, U.S. Pat. No. 6,127,600 (method of increasing accumulation of essential amino acids in seeds), U.S. Pat. No. 6,080,913 (binary methods of increasing accumulation of essential amino acids in seeds), U.S. Pat. No. 5,990,389 (high lysine), WO99/40209 (alteration of amino acid compositions in seeds), WO99/29882 (methods for altering amino acid content of proteins), U.S. Pat. No. 5,850,016 (alteration of amino acid compositions in seeds), WO 98/20133 (proteins with enhanced levels of essential amino acids), U.S. Pat. No. 5,885,802 (high methionine), U.S. Pat. No. 5,885,801 (high threonine), U.S. Pat. No. 6,664,445 (plant amino acid biosynthetic enzymes), U.S. Pat. No. 6,45,9019 (increased lysine and threonine), U.S. Pat. No. 6,441,274 (plant tryptophan synthase beta subunit), U.S. Pat. No. 6,346,403 (methionine metabolic enzymes), U.S. Pat. No. 5,939,599 (high sulfur), U.S. Pat. No. 5,912,414 (increased methionine), WO98/56935 (plant amino acid biosynthetic enzymes), WO98/45458 (engineered seed protein having higher percentage of essential amino acids), WO98/42831 (increased lysine), U.S. Pat. No. 5,633,436 (increasing sulfur amino acid content), U.S. Pat. No. 5,559,223 (synthetic storage proteins with defined structure containing programmable levels of essential amino acids for improvement of the nutritional value of plants), WO96/01905 (increased threonine), WO95/15392 (increased lysine), US2003/0163838, US2003/0150014, US2004/0068767, US6803498, WO01/79516, and WO00/09706 (Ces A: cellulose synthase), U.S. Pat. No. 6,194,638 (hemicellulose), U.S. Pat. No. 6,399,859 and US2004/0025203 (UDPGdH), U.S. Pat. No. 6,194,638 (RGP).

4. Genes that Control Pollination, Hybrid Seed Production or Male-Sterility

There are several methods of conferring genetic male sterility available, such as multiple mutant genes at separate locations within the genome that confer male sterility, as disclosed in U.S. Pat. Nos. 4,654,465 and 4,727,219 to Brar, et al., and chromosomal translocations as described by Patterson in U.S. Pat. Nos. 3,861,709 and 3,710,511. In addition to these methods, Albertsen, et al., U.S. Pat. No. 5,432,068, describe a system of nuclear male sterility which includes: identifying a gene which is critical to male fertility; silencing this native gene which is critical to male fertility; removing the native promoter from the essential male fertility gene and replacing it with an inducible promoter; inserting this genetically engineered gene back into the plant; and thus creating a plant that is male sterile because the inducible promoter is not "on" resulting in the male fertility gene not being transcribed. Fertility is restored by inducing, or turning "on", the promoter, which in turn allows the gene that confers male fertility to be transcribed.

(A) Introduction of a deacetylase gene under the control of a tapetum-specific promoter and with the application of the chemical N-Ac-PPT (WO 01/29237).

(B) Introduction of various stamen-specific promoters (WO 92/13956, WO 92/13957).

(C) Introduction of the barnase and the barstar gene (Paul, et al., (1992) *Plant Mol. Biol.* 19:611-622).

For additional examples of nuclear male and female sterility systems and genes, see also, U.S. Pat. No. 5,859,341; U.S. Pat. No. 6,297,426; U.S. Pat. No. 5,478,369; U.S. Pat. No. 5,824,524; U.S. Pat. No. 5,850,014; and U.S. Pat. No. 6,265,640; all of which are hereby incorporated by reference.

Also see, U.S. Pat. No. 5,426,041 (invention relating to a method for the preparation of a seed of a plant comprising crossing a male sterile plant and a second plant which is male fertile), U.S. Pat. No. 6,013,859 (molecular methods of hybrid seed production) and U.S. Pat. No. 6,037,523 (use of male tissue-preferred regulatory region in mediating fertility), all of which are hereby incorporated by reference for this purpose.

5. Genes that Create a Site for Site Specific DNA Integration

This includes the introduction of FRT sites that may be used in the FLP/FRT system and/or Lox sites that may be used in the Cre/Loxp system. For example, see, Lyznik, et al., Site-Specific Recombination for Genetic Engineering in Plants, *Plant Cell Rep* (2003) 21:925-932 and WO 99/25821, which are hereby incorporated by reference. Other systems that may be used include the Gin recombinase of phage Mu (Maeser, et al., 1991), the Pin recombinase of *E. coli* (Enomoto, et al., 1983), and the R/RS system of the pSR1 plasmid (Araki, et al., 1992).

6. Genes that affect abiotic stress resistance (including but not limited to flowering, seed development, enhancement of nitrogen utilization efficiency, altered nitrogen responsiveness, drought resistance or tolerance, cold resistance or tolerance, and salt resistance or tolerance) and increased yield under stress. For example, see, WO 00/73475 where water use efficiency is altered through alteration of malate; U.S. Pat. No. 5,892,009, U.S. Pat. N. 5,965,705, U.S. Pat. No. 5,929,305, U.S. Pat. No. 5,891,859, U.S. Pat. No. 6,417,428, U.S. Pat. No. 6,664,446, U.S. Pat. No. 6,706,866, U.S. Pat. No. 6,717,034, U.S. Pat. No. 6,801,104, WO2000060089, WO2001026459, WO2001035725, WO2001034726, WO2001035727, WO2001036444, WO2001036597, WO2001036598, WO2002015675, WO2002017430, WO2002077185, WO2002079403, WO2003013227, WO2003013228, WO2003014327, WO2004031349, WO2004076638, WO9809521, and WO9938977 describing genes, including CBF genes and transcription factors effective in mitigating the negative effects of freezing, high salinity, and drought on plants, as well as conferring other positive effects on plant phenotype; US2004/0148654 and WO01/36596 where abscisic acid is altered in plants resulting in improved plant phenotype such as increased yield and/or increased tolerance to abiotic stress; WO2000/006341, WO04/090143, U.S. application Ser. Nos. 10/817,483 and 09/545,334 where cytokinin expression is modified resulting in plants with increased stress tolerance, such as drought tolerance, and/or increased yield. Also see, WO0202776, WO2003052063, JP2002281975, U.S. Pat. No. 6,084,153, WO0164898, U.S. Pat. No. 6,177,275, and U.S. Pat. No. 6,107,547 (enhancement of nitrogen utilization and altered nitrogen responsiveness). For ethylene alteration, see US20040128719, US20030166197 and WO200032761. For plant transcription factors or transcriptional regulators of abiotic stress, see, e.g., US20040098764 or US20040078852.

Other genes and transcription factors that affect plant growth and agronomic traits such as yield, flowering, plant growth and/or plant structure, can be introduced or introgressed into plants, see e.g., WO97/49811 (LHY), WO98/56918 (ESD4), WO97/10339 and U.S. Pat. No. 6,573,430 (TFL), U.S. Pat. No. 6,713,663 (FT), WO96/14414 (CON), WO96/38560, WO01/21822 (VRN1), WO00/44918 (VRN2), WO99/49064 (GI), WO00/46358 (FRI), WO97/29123, U.S. Pat. No. 6,794,560, U.S. Pat. No. 6,307,126 (GAI), WO99/09174 (D8 and Rht), and WO2004076638 and WO2004031349 (transcription factors).

Although it is a hybrid, 46P50 is ideal breeding material for the high oil trait. For example, it can be self pollinated to produce new high oil restorer inbred lines or it can be crossed with female pool germplasm to transfer the high oil trait. Accordingly, the invention comprises any progeny, descendent, sub-line or offspring derived from 46P50 or from a line obtained by crossing 46P50 to a second *Brassica* plant. The invention also includes any doubled haploid lines derived from 46P50, or from a tissue culture of 46P50.

Further, as is known to those skilled in the art, the hybrid seed and plant thereof can be used to grow a *Brassica* crop. The method used to grow the crop may include sowing seed designated 46P50 and having ATCC accession number PTA-8304, or a descendent, a sub-line, or from a plant produced by crossing 46P50 with a second plant; under *Brassica* growing conditions and growing the resultant plant under *Brassica* growing conditions.

The seed of the 46P50 hybrid, the plant produced from such seed, and various parts of the hybrid canola plant can be utilized in the production of an edible vegetable oil or other food products in accordance with known techniques. The remaining solid meal component derived from seeds can be used as a nutritious livestock feed. For example, seed harvested from the hybrid plant (i.e. F2 seed) can be crushed and used for oil and/or meal production. The method used for producing oil may comprise the steps of crushing seed produced by a plant line designated 46P50 and having ATCC accession number PTA-8304, or a descendent, a sub-line, or from a plant produced by crossing 46P50 with a second plant and extracting oil from said crushed seeds. The method may further comprise the step of refining, bleaching and deodorizing said oil.

Also encompassed in the Applicant's teachings is a *Brassica* canola grain having an average percent oil of between about 51% and 52%, the grain harvested from a commercial *Brassica* hybrid, grown over multiple locations and over many environments, wherein reference varieties 46A65 and Q2 yield a grain with an average percent oil of about 48% to 49% over these same locations and environments, and wherein the percent oil is calculated at 0% moisture and the percent protein in the hybrid grain is not compromised by the high oil. Oil from this grain is also encompassed in the Applicant's teachings.

Crushed seed from 46P50, or a descendent, a sub-line, or from a plant produced by crossing 46P50 with a second plant is also encompassed in the Applicant's teaching. Canola oil obtained from an F2 seed, harvested from a *Brassica* hybrid plant designated 46P50, hybrid seed of which were deposited under ATCC accession number PTA-8304, or a descendent, a sub-line, or from a plant produced by crossing 46P50 with a second plant, wherein the F2 seed has between about a 2.7% to 3.3% percent by weight increase in oil present in the mature whole dried seed when compared with the average oil per gram of seed of 46A65 and Q2 when grown under the same environmental conditions, and when calculated at 0% moisture, is also encompassed in the invention. Accordingly, the seed can have between about 2.8% to 3.2%, or between about 2.9% and 3.1%, or about 3% increase in oil when calculated at 0% moisture.

Also included in the Applicant's teaching is a *Brassica* seed having an average of about 2.7% to 3.3% percent by weight increase in oil present in the mature whole dried seed when compared with the average oil per gram of seed of 46A65 and Q2 when grown under the same environmental conditions, and wherein the percent oil is calculated at 0% moisture. Accordingly, a seed having between about 2.8% to 3.2%, 2.9% to 3.1% and about 3% is also included in the Applicant's teaching.

Commercialization

The consistent high oil content will allow growers to charge a premium per tonne for the grain produced from the 46P50 hybrid. Lately the use of biodiesel has increased, therefore canola varieties with higher oil are in demand. This hybrid is unique because it is not only high in oil content but also high in protein, high yielding, glyphosate resistant, and disease resistant (blackleg and *fusarium*).

Deposits

Applicant(s) have made a deposit of at least 2500 seeds of Canola Cultivar 46P50 with the American Type Culture Collection (ATCC), Manassas, Va. 20110-2209 USA, ATCC Deposit No. PTA-8304. The seeds deposited with the ATCC on Apr. 2, 2007 were taken from the deposit maintained by Pioneer Hi-Bred International, Inc., 7250 NW 62$^{nd}$ Avenue, Johnston, Iowa 50131 since prior to the filing date of this application. Access to this deposit will be available during the pendency of the application to the Commissioner of Patents and Trademarks and persons determined by the Commissioner to be entitled thereto upon request. Upon grant of the patent herein applied for, the Applicant will make the deposit available to the public pursuant to 37 C.F.R. §1.808. This deposit of Canola Variety 46P50 will be maintained in the ATCC depository, which is a public depository, for a period of 30 years, or 5 years after the most recent request, or for the enforceable life of the patent, whichever is longer, and will be replaced if it becomes nonviable during that period. Additionally, Applicant has or will satisfy all the requirements of 37 C.F.R. §§1.801-1.809, including providing an indication of the viability of the sample upon deposit. Applicant has no authority to waive any restrictions imposed by law on the transfer of biological material or its transportation in commerce. Applicant does not waive any infringement of their rights granted under this patent or under the Plant Variety Protection Act (7 USC 2321 et seq.).

The foregoing invention has been described in detail by way of illustration and example for purposes of exemplification. However, it will be apparent that changes and modifications such as single gene modifications and mutations, somaclonal variants, variant individuals selected from populations of the plants of the instant cultivar, and the like, likewise are considered to be within the scope of the present invention.

All references cited in the Applicant's teaching are herein incorporated by reference.

Although the invention has been described with certain embodiments, it is to be understood that variations and modifications may be resorted to as will be apparent to those skilled in the art. Such variations and modifications are to be considered within the purview and scope of the claims appended hereto.

What is claimed is:

1. A Brassica seed or plant thereof designated 46P50, representative seed of which have been deposited under ATCC Accession No. PTA-8304, or an F1 progeny plant produced by crossing 46P50 with a second plant, wherein said F1 progeny plant yields seeds wherein the average weight of oil per gram of mature whole dried seed is 2.7 to 3.3 percentage points higher than the average weight of oil per gram of mature whole dried seed produced by 46A65 or Q2 when grown under the same environmental conditions.

2. The *Brassica* seed or plant thereof of claim 1 wherein the seed or plant is 46P50.

3. The *Brassica* seed or plant thereof of claim 1 wherein the seed or plant is an F1 progeny plant.

4. The *Brassica* seed or plant thereof of claim 1 wherein the seed or plant is produced by crossing 46P50 with a second plant.

5. The *Brassica* plant of claim 1 wherein the average weight of oil per gram of mature whole dried seed harvested from said plant is 2.7 to 3.3 percentage points higher than the average weight of oil per gram of mature whole dried seed of 46A65 or Q2 when grown under the same environmental conditions.

6. The *Brassica* plant of claim 1 or 5 wherein the average weight of oil per gram of mature whole dried seed harvested from said plant is about 3.0 percentage points higher than the average weight of oil per gram of mature whole dried seed produced by 46A65 or Q2 when grown under the same environmental conditions.

7. The *Brassica* seed or plant of claim 1 wherein the seed or plant is glyphosate resistant.

8. The *Brassica* seed or plant of claim 1 wherein the seed or plant is blackleg resistant.

9. The *Brassica* seed or plant of claim 1 further comprising at least one transgene other than the glyphosate resistance gene from RT73 event.

10. A process of growing a crop comprising the steps of:
  (a) planting the *Brassica* seed designated 46P50, representative seed of which have been deposited under ATCC Accession No. PTA-8304, or seed produced by crossing 46P50 with a second plant;
  (b) growing a seed of (a) into a *Brassica* plant in the field under conventional oilseed *Brassica* growing conditions;
  (c) producing *Brassica* seeds from the plant of (b); and optionally
  (d) harvesting the resultant *Brassica* crop.

11. A plant part of the plant of claim 1.

12. A method of producing oil and/or meal, comprising the steps of:
  (a) crushing seeds produced by a plant line designated 46P50, representative seed of which have been deposited under ATCC Accession No. PTA-8304, or an F1 progeny plant produced by crossing 46P50 with a second plant wherein said F1 progeny plant yields seeds wherein the average weight of oil per gram of mature whole dried seed is 2.7 to 3.3 percentage points higher than the average weight of oil per gram of mature whole dried seed produced by 46A65 or Q2 when grown under the same environmental conditions; and
  (b) extracting oil and/or meal from said crushed seeds.

13. A method of breeding a plant line, comprising the steps of:
  (a) crossing a first plant designated 46P50 and having ATCC accession number PTA-8304, with itself or a second *Brassica* plant to produce an F1 progeny plant; and
  (b) selecting at least one plant of said cross.

14. The method of claim 13 wherein the selected plant of said cross produces a seed wherein the average weight of oil per gram of mature whole dried seed is about 3.0 percentage points higher than the average weight of oil per gram of mature whole dried seed produced by 46A65 or Q2 when grown under the same environmental conditions.

15. The method according to claim 13, wherein said F1 progeny plant is further used in a breeding program selected from the group consisting of pedigree breeding, self-pollination, haploidy, single seed descent, modified single seed descent, and backcrossing followed by selecting at least one plant of said cross.

16. A tissue culture of regenerable cells of a *Brassica* plant thereof designated 46P50, representative seed of which have been deposited under ATCC Accession No. PTA-8304, or a tissue culture of an F1 progeny plant produced by crossing 46P50 with a second plant.

17. A *Brassica* plant produced from the tissue culture of claim 16.

18. A plant cell of a *Brassica* seed or plant thereof designated 46P50, representative seed of which have been deposited under ATCC Accession No. PTA-8304, or of an F1 progeny plant produced by crossing 46P50 with a second plant.

19. A Brassica napus F1 progeny plant seed of variety 46P50, representative seed of which have been deposited under ATCC Accession No. PTA-8304, wherein the average weight of oil per gram of mature whole dried seed harvested from said progeny plant is 2.7 to 3.3 percentage points higher than the average weight of oil per gram of whole mature dried seed of 46A65 or Q2 when grown under the same environmental conditions.

20. A cell of an F1 progeny plant of 46P50, representative seed of which have been deposited under ATCC Accession No. PTA-8304, wherein the average weight of oil per gram of mature whole dried seed harvested from said progeny plant is 2.7 to 3.3 percentage points higher than the average weight of oil per gram of mature whole dried seed of 46A65 or Q2 when grown under the same environmental conditions.

21. An inbred progeny *Brassica* plant produced by self pollinating 46P50, representative seed of which have been deposited under ATCC Accession No. PTA-8304, wherein said inbred progeny *Brassica* plant yields seeds wherein the average weight of oil per gram of mature whole dried seed is 2.7 to 3.3 percentage points higher than the average weight of oil per gram of mature whole dried seed produced by 46A65 or Q2 when grown under the same environmental conditions.

22. A haploid *Brassica* embryo or plant produced by isolating microspores from the *Brassica* plant of claim 1 and culturing the isolated microspores to induce embryogenesis.

23. A doubled haploid *Brassica* embryo or plant produced by doubling the chromosomes of the haploid *Brassica* embryo or plant of claim 22.

* * * * *